United States Patent
Masjedizadeh et al.

(10) Patent No.: US 11,369,613 B2
(45) Date of Patent: Jun. 28, 2022

(54) SALTS AND SOLID FORM OF A BTK INHIBITOR

(71) Applicant: PRINCIPIA BIOPHARMA INC., South San Francisco, CA (US)

(72) Inventors: Mohammad Reza Masjedizadeh, San Jose, CA (US); Steven Gourlay, Queens Park (AU)

(73) Assignee: Principia Biopharma Inc., South San Francisco, CA (US)

( * ) Notice: Subject to any disclaimer, the term of this patent is extended or adjusted under 35 U.S.C. 154(b) by 0 days.

(21) Appl. No.: 17/063,061

(22) Filed: Oct. 5, 2020

(65) Prior Publication Data

US 2021/0015821 A1 Jan. 21, 2021

Related U.S. Application Data

(60) Division of application No. 16/596,611, filed on Oct. 8, 2019, now Pat. No. 10,828,307, which is a continuation of application No. 16/116,425, filed on Aug. 29, 2018, now Pat. No. 10,456,403, which is a continuation of application No. 15/120,293, filed as application No. PCT/US2015/016963 on Feb. 20, 2015, now Pat. No. 10,092,569.

(60) Provisional application No. 62/096,468, filed on Dec. 23, 2014, provisional application No. 61/946,480, filed on Feb. 28, 2014, provisional application No. 61/943,262, filed on Feb. 21, 2014.

(51) Int. Cl.
  *A61K 31/519* (2006.01)
  *A61K 31/5395* (2006.01)
  *A61P 25/00* (2006.01)
  *A61K 45/06* (2006.01)
  *C07D 487/04* (2006.01)

(52) U.S. Cl.
  CPC ........ *A61K 31/519* (2013.01); *A61K 31/5395* (2013.01); *A61K 45/06* (2013.01); *A61P 25/00* (2018.01); *C07D 487/04* (2013.01)

(58) Field of Classification Search
  CPC ...... A61K 31/519; C07D 487/04; A61P 35/00
  USPC ........................................ 514/262.1; 544/262
  See application file for complete search history.

(56) References Cited

U.S. PATENT DOCUMENTS

| | | |
|---|---|---|
| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,828,426 B2 | 9/2014 | Shah et al. |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens et al. |
| 9,994,576 B2 | 6/2018 | Owens et al. |
| 10,092,569 B2 | 10/2018 | Masjedizadeh et al. |
| 10,456,403 B2 | 10/2019 | Masjedizadeh et al. |
| 10,485,797 B2 | 11/2019 | Gourlay |
| 10,533,013 B2 | 1/2020 | Owens et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |

(Continued)

FOREIGN PATENT DOCUMENTS

| | | |
|---|---|---|
| CN | 1274280 A | 11/2000 |
| CN | 1681483 A | 10/2005 |

(Continued)

OTHER PUBLICATIONS

2012 ICD-9-CM Diagnosis Code 372.30: Conjunctivitis, unspecified, retrieved Aug. 4, 2016 (1 page).

(Continued)

*Primary Examiner* — Jeffrey H Murray

(74) *Attorney, Agent, or Firm* — McNeill Baur PLLC

(57) ABSTRACT

Disclosed herein are processes for preparing 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile free base (compound (I)), salts of compound (I) and solid state form of said salts. Also disclosed herein are pharmaceutical compositions comprising such salts and solid state form thereof and methods of treating cancer, autoimmune, and inflammatory diseases using compound (I) or a pharmaceutically acceptable salt thereof.

3 Claims, 17 Drawing Sheets

(56) References Cited

U.S. PATENT DOCUMENTS

| | | |
|---|---|---|
| 2006/0079494 A1 | 4/2006 | Santi et al. |
| 2006/0275376 A1 | 12/2006 | Guimberteau et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2013/0079327 A1 | 3/2013 | Yamamoto et al. |
| 2013/0197014 A1 | 8/2013 | Chen et al. |
| 2014/0094459 A1 | 4/2014 | Goldstein et al. |
| 2014/0142099 A1 | 5/2014 | Owens |
| 2014/0221398 A1 | 8/2014 | Goldstein et al. |
| 2014/0256734 A1 | 9/2014 | Lawson et al. |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0257686 A1 | 9/2016 | Owens |
| 2016/0376277 A1 | 12/2016 | Desai et al. |
| 2018/0015088 A1 | 1/2018 | Nunn et al. |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2019/0231784 A1 | 8/2019 | Ferdous et al. |
| 2019/0345159 A1 | 11/2019 | Goldstein et al. |
| 2020/0038405 A1 | 2/2020 | Masjedizadeh et al. |
| 2020/0101059 A1 | 4/2020 | Gourlay et al. |
| 2020/0190092 A1 | 6/2020 | Owens et al. |

FOREIGN PATENT DOCUMENTS

| | | |
|---|---|---|
| CN | 1874761 A | 12/2006 |
| CN | 101610676 A | 12/2009 |
| CN | 101730699 A | 6/2010 |
| CN | 101805341 A | 8/2010 |
| CN | 101880243 A | 11/2010 |
| CN | 102159214 A | 8/2011 |
| CN | 103096716 A | 5/2013 |
| CN | 103534258 A | 1/2014 |
| CN | 104640861 A | 5/2015 |
| CN | 105753863 A | 7/2016 |
| EP | 0461546 A2 | 12/1991 |
| EP | 0493767 A2 | 7/1992 |
| EP | 0908457 A1 | 4/1999 |
| EP | 2443929 A1 | 4/2012 |
| EP | 2578585 A1 | 4/2013 |
| FR | 2535721 A1 | 5/1984 |
| GB | 2447933 A | 10/2008 |
| JP | 56-63950 A | 5/1981 |
| JP | 02-1450 A | 1/1990 |
| JP | 04-177244 A | 6/1992 |
| JP | 2005-239657 A | 9/2005 |
| JP | 2010-504324 A | 2/2010 |
| JP | 2010-235628 A | 10/2010 |
| JP | 2014-513729 A | 6/2014 |
| JP | 2014-517838 A | 7/2014 |
| JP | 6203848 | 9/2017 |
| WO | WO 95/24190 A2 | 9/1995 |
| WO | WO 95/31432 A1 | 11/1995 |
| WO | WO 98/41499 A1 | 9/1998 |
| WO | WO 99/14216 A1 | 3/1999 |
| WO | WO 99/18938 | 4/1999 |
| WO | WO 01/72751 A1 | 10/2001 |
| WO | WO 02/066463 A1 | 8/2002 |
| WO | WO 03/037890 A2 | 5/2003 |
| WO | WO 03/050080 A1 | 6/2003 |
| WO | WO 03/068157 A2 | 8/2003 |
| WO | WO 03/082807 A2 | 10/2003 |
| WO | WO 2004/016259 A1 | 2/2004 |
| WO | WO 2004/074283 A1 | 9/2004 |
| WO | WO 2005/020929 A2 | 3/2005 |
| WO | WO 2005/023773 A1 | 3/2005 |
| WO | WO 2005/030184 A2 | 4/2005 |
| WO | WO 2005/085210 A1 | 9/2005 |
| WO | WO 2006/086634 A2 | 8/2006 |
| WO | WO 2006/134468 A1 | 12/2006 |
| WO | WO 2007/043401 A1 | 4/2007 |
| WO | WO 2007/087068 A2 | 8/2007 |
| WO | WO 2007/130075 A1 | 11/2007 |
| WO | WO 2007/142755 A2 | 12/2007 |
| WO | WO 2008/005954 A2 | 1/2008 |
| WO | WO 2008/006032 A1 | 1/2008 |
| WO | WO 2008/039218 A2 | 4/2008 |
| WO | WO 2008/054827 A2 | 5/2008 |
| WO | WO 2008/061740 A1 | 5/2008 |
| WO | WO 2008/072053 A2 | 6/2008 |
| WO | WO 2008/072077 A2 | 6/2008 |
| WO | WO 2008/116064 A2 | 9/2008 |
| WO | WO 2008/121742 A2 | 10/2008 |
| WO | WO 2009/140128 A2 | 11/2009 |
| WO | WO 2009/143477 A1 | 11/2009 |
| WO | WO 2010/009342 A2 | 1/2010 |
| WO | WO 2010/014930 A2 | 2/2010 |
| WO | WO 2010/065898 A2 | 6/2010 |
| WO | WO 2011/031896 A2 | 3/2011 |
| WO | WO 2011/046964 A2 | 4/2011 |
| WO | WO 2011/060440 A2 | 5/2011 |
| WO | WO 2011/144585 A1 | 11/2011 |
| WO | WO 2011/152351 A1 | 12/2011 |
| WO | WO 2011/153514 A2 | 12/2011 |
| WO | WO 2012/021444 A1 | 2/2012 |
| WO | WO 2012/158764 A1 | 11/2012 |
| WO | WO 2012/158795 A1 | 11/2012 |
| WO | WO 2012/158810 A1 | 11/2012 |
| WO | WO 2012/158843 A2 | 11/2012 |
| WO | WO 2013/003629 A2 | 1/2013 |
| WO | WO 2013/010136 A2 | 1/2013 |
| WO | WO 2013/010380 A1 | 1/2013 |
| WO | WO 2013/010868 A1 | 1/2013 |
| WO | WO 2013/010869 A1 | 1/2013 |
| WO | WO 2013/041605 A1 | 3/2013 |
| WO | WO 2013/059738 A1 | 4/2013 |
| WO | WO 2013/102059 A1 | 7/2013 |
| WO | WO 2013/116382 A1 | 8/2013 |
| WO | WO 2013/185082 A2 | 12/2013 |
| WO | WO 2013/191965 A1 | 12/2013 |
| WO | WO 2014/004707 A1 | 1/2014 |
| WO | WO 2014/022569 A1 | 2/2014 |
| WO | WO 2014/039899 A1 | 3/2014 |
| WO | WO 2014/068527 A1 | 5/2014 |
| WO | WO 2014/078578 A1 | 5/2014 |
| WO | WO 2014/164558 A1 | 10/2014 |
| WO | WO 2015/127310 A1 | 8/2015 |
| WO | WO 2015/132799 A2 | 9/2015 |
| WO | WO 2017/041536 A1 | 3/2017 |
| WO | WO 2017/066014 A1 | 4/2017 |

OTHER PUBLICATIONS

Abstract for Neplyuev, V.M. (1979), "Studies of triacylmethanes VII. 1,1,3,3-Tetraacyl-3-arylazo-1-propenes," *Zhurnal Organicheskoi Khimii*, 15(3): 563-566 (1 page).

Abstract for Neplyuev, V.M. (1983), "Nitration and nitrosation of 1,1,3,3-tetraacyl-1-propenes" *Ukrainskii Khimicheskii Zhurnal (Russian Edition)*, 49(2):192-194 (1 page).

(56) References Cited

OTHER PUBLICATIONS

Abdulahad, W.H. et al. (2012), "Immune regulation and B-cell depletion therapy in patients with primary Sjögren's syndrome," *J. Autoimmun*, 39(1): 103-111 (2012).

American Cancer Society. Can Non-Hodgkin's Lymphoma Be Prevented? (2016) Web: <https://www.cancer.org/cancer/non-hodgkin-lymphoma/causes-risks-- prevention/prevention.html> (3 pages).

Ansel, H.C. et al., "Pharmaceutical Dosage Forms and Drug Delivery Systems," Seventh Edition, Lippincott Williams & Wilkins, A Wolters Kluwer Company, Chapters 1-8, pp. 1-243 (1999).

Armesto, D. et al. (2010), "Efficient photochemical synthesis of 2-vinylcyclopropanecarbaldehydes, precursors of cyclopropane components present in pyrethroids, by using the oxa-di-π-methane rearrangement," *Tetrahedron*, 66: 8690-8697.

Arnold, L.D. et al. (2000), "Pyrrolo[2,3-d]pyrimidines Containing an Extended 5-Substituent as Potent and Selective Inhibitors of lck I," *Bioorg. Med. Chem. Lett.*, 10:2167-2170.

Arora, A. & E.M. Scholar (2005), "Role of Tyrosine Kinase Inhibitors in Cancer Therapy," *J. Pharmacol. Exp. Ther.*, 315(3):971-979.

Basheer, A. et al. (2007), "Enols of Substituted Cyanomalonamides," *J. Org. Chem.* 72:5297-5312.

Bastin, R.J. et al. (2000), "Salt Selection and Optimisation Procedures for Pharmaceutical New Chemical Entities," *Org. Process Res. Dev*, 4:427-435.

Berge, S.M. et al. (1977), "Pharmaceutical Salts," *J. Pharm. Sci.*, 66:1-19.

Bernhart, C.A. et al. (1983), "Synthesis and Antiarrhythmic activity of New [(Dialkylamino)alkyl]pyridylacetamides," *J. Med. Chem.*, 26:451-455.

Bradshaw, J. et al. (2015) "Prolonged and tunable residence time using reversible covalent kinase inhibitors," *Nat. Chem. Biol.*, 11:525-531 (with online methods) (10 pages).

Burchat, A.F. et al. (2000), "Pyrrolo[2,3-d]pyrimidines Containing an Extended 5-Substituentas Potent and Selective Inhibitors of lck II," *Bioorg. Med. Chem. Lett*, 10:2171-2174.

Burini, E. et al. (2005), "Efficient Synthesis of 4-Cyano 2,3-Dihydrooxazoles by Direct Amination of 2-Alkylidene 3-Oxo Nitriles," *Synlett*, 17: 2673-2675.

Calderwood, D.J. et al. (2002), "Pyrrolo[2,3-d]pyrimidines Containing Diverse N-7 Substituents as Potent Inhibitors of Lck," *Bioorg. Med. Chem. Lett.*, 12:1683-1686.

CAS RN 26272-41-3, STN entered Nov. 16, 1984 (1 page).

Certified English Translation of CN 105753863 A, published in Chinese on Jul. 13, 2016 (57 pages).

Cohen, M.S. et al. (2005), "Structural Bioinformatics-Based Design of Selective, Irreversible Kinase Inhibitors," *Science*, 308:1318-1321.

Deng, Y.-R. et al. (2013), "Reversible phospho-Smad3 signalling between tumour suppression and fibrocarcinogenesis in chronic hepatitis B infection," *Clin. Exp. Immunol.*, 176:102-111.

Dias, A.L. & D. Jain (2013), "Ibrutinib: A New Frontier in the Treatment of Chronic Lymphocytic Leukemia by Bruton's Tyrosine Kinase Inhibition," *Cardiovasc Hematol Agents Med Chem.*, 11(4):265-271.

Di Paolo, J.A. et al. (2011), "Specific Btk inhibition suppresses B cell- and myeloid cell-mediated arthritis," *Nat. Chem. Biol.*, 7:41-50.

Donald, A. et al. (2007), "Rapid Evolution of 6-Phenylpurine Inhibitors of Protein Kinase B through Structure-Based Design," *J. Med. Chem.*, 50:2289-2292.

Elinson, M.N. et al. (1998), "Electrochemical transformation of cyanoacetic ester and alkylidenecyanoacetic esters into 3-substituted 1,2-dicyanocyclopropane-1,2-dicarboxylates," *Russian Chemical Bulletin*, 47(6):1133-1136.

Elliott, M. et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry (1972-1999) (1974), (21), 2470-2474.

Elliott, M. et al. (1976), "Insecticidal activity of the Pyrethrins and Related Compounds X.[a] 5-Benzyl-3-furylmethyl 2,2-dimethylcyclopropanecarboxylates with ethylenic substituents at position 3 on the cyclopropane ring," *Pestic. Sci.*, 7: 499-502.

English Language Abstract for JP 42008308 B4, published Apr. 8, 1967, by Yoshitomi Pharmaceutical Industries, Ltd. (1 page).

Evans, E.K. et al. (2013), "Inhibition of Btk with CC-292 Provides Early Pharmacodynamic Assessment of Activity in Mice and Humans,"*J. Pharm. Exp. Ther.*, 346(2):219-28.

Fioravanti, S. et al. (2006), "Parallel Solution-Phase Synthesis of Acrylonitrile Scaffolds Carrying $_L$-α-Amino Acidic or D-Glycosyl Residues," *J. Comb. Chem.*, 8: 808-811.

Ghoreschi, K. et al. (2009), "Janus kinases in immune cell signaling," *Immunol Rev.*, 228:273-287.

Grando, S.A. (2012), "Pemphigus autoimmunity: Hypotheses and realities," *Autoimmunity*, 45(1):7-35.

Gyoung, Y.S. et al. (2000), "Regiospecific synthesis of 2-allylated-5-substituted tetrazoles via palladium-catalyzed reaction of nitriles, trimethylsilyl azide, and allyl acetates," *Tetrahedron Lett.*, 41(21): 4193-4196.

Hackam, D.G. & D.A. Redelmeier (2006), "Translation of Research Evidence from Animals to Humans," JAMA, 296(14):1731-1732.

Hantschel, O. et al. (2007), "The Btk tyrosine kinase is a major target of the Bcr-Abl inhibitor dasatinib." *PNAS*, 104(33): 13283-13288.

Honigberg, L.A. et al. (2010), "The Bruton tyrosine kinase inhibitor PCI-32765 blocks B-cell activation and is efficacious in models of autoimmune disease and B-cell malignacy," *PNAS*, 107(29):13075-13080.

Jenner, G. (2001), "Steric effects in high pressure Knoevenagel reactions," *Tetrahedron Lett.*, 42(2): 243-245.

Johnson, M. & K.J. Corcoran, "Coding for Dry Eye," Optometric Management, Issue: Mar. 2004 (7 pages).

Jordan, V.C. (2003), "Tamoxifen: A Most Unlikely Pioneering Medicine," *Nat. Rev. Drug Discov.*, 2:205-213.

Kamath, S. & Buolamwini J.K. (2003), "Receptor-Guided Alignment-Based Comparative 3D-QSAR Studies of Benzylidene Malonitrile Tyrphostins as EGFR and HER-2 Kinase Inhibitors," *J. Med. Chem.*, 46:4657-4668.

Kamijo, S. et al. (2003), "Tetrazole synthesis via the palladium-catalyzed three component coupling reaction," *Molecular Diversity*, 6:181-192.

Kanwar, A.J. & K. Vinay (2012), "Rituximab in Pemphigus," Indian J. Dermatol. Venereol. Leprol. [serial online], 78:671-676, http://www.ijdvl.com/text.asp?2012/78/6/671/102354 (10 pages).

Knight, Z.A. et al. (2007), "A membrane capture assay for lipid kinase activity," *Nat. Protoc.*, 2(10):2459-2466.

Kojima, S. et al. (2004), "Stereoselective synthesis of activated cyclopropanes with an α-pyridinium acetamide bearing an 8-phenylmenthyl group as the chiral auxiliary," *Tetrahedron Lett.*, 45(18): 3565-3568.

Komura, K. et al. (2007), "Layered silicate PLS-1: A new solid base catalyst for C—C bond forming reactions," *Catal Common.*, 8(4): 644-648.

Kotz, A. & W. Zorning, "The Action of Chloroform on Methylene and Methenyl Groups," *Journal fuer Praktische Chemie (Leipzig)*, Abstract, 74: 425-48 (1907).

Leopold, C.S., "A Practical Approach in the Design of Colon-specific Drug Delivery System," Wiley-VCH; Drug Targeting Organ-Specific Strategies, Chapter 6, pp. 157-170 (2001).

Li Zhensu, Medicinal Chemistry, Chemical Industry Press, China, Mar. 3, 1981, pp. 435-436 (2 pages).

Lou, Y. et al. (2012), "Bruton's Tyrosine Kinase Inhibitors: Approaches to Potent and Selective Inhibition, Preclinical and Clinical Evaluation for Inflammatory Diseases and B Cell Malignancies," *J. Med. Chem.*, 55(10): 4539-4550.

Maas, S. et al. (1999), "Conjugate Addition of Dialkylaluminum Chlorides to Alkylidenemalonic Acid Derivatives," *Synthesis*, 10:1792-1798.

Maurya, R.A. et al. (2013), "Catalyst-free stereoselective cyclopropanation of electron deficient alkenes with ethyl diazoacetate," *RSC Adv.*, 3:15600-15603.

(56) References Cited

OTHER PUBLICATIONS

MedicineNet.com. Definition of Cancer. (2004) Web: <http://www.medterms.com> (1 page).
MedlinePlus. Autoimmune Diseases (2014) Web: <https://www.nlm.nih.gov/medlineplus/autoimmunediseases.html> (5 pages).
Meydan, N. et al. (1996), "Inhibition of acute lymphoblastic leukaemia by a Jak-2 inhibitor," *Nature*, 379:645-648.
Nakamura, M. et al. (2012), "Diquafosol Ophthalmic Solution for Dry Eye Treatment," *Adv Ther*, 29(7):579-589.
Pan, Z. et al. (2007), "Discovery of Selective Irreversible Inhibitors for Bruton's Tyrosine Kinase," *ChemMedChem*, 2:58-61.
Patani, G. & E. Lavoie (1996), "Bioisosterism: A Rational Approach in Drug Design," *Chem. Rev.*, 96:3147-3176.
Pennington, L.D. et al., "The Necessary Nitrogen Atom: A Versatile High-Impact Design Element for Multiparameter Optimization," *J. Med. Chem.*, ePub Feb. 8, 2017, 28 pages, DOI: 10.1021/acs.jmedchem.6b01807.
Porter, D.W. et al. (2014), "The discovery of potent, orally bioavailable pyrimidine-5-carbonitrile-6-alkyl CXCR2 receptor antagonists," *Bioorg. Med. Chem. Lett.*, 24: 3285-3290.
Proenca, F. & Costa, M. (2008), "A simple and eco-friendly approach for the synthesis of 2-imino and 2-oxo-2H-chromene-3-carboxamides," *Green Chem.*, 10:995-998.
Rankin, A.L. et al. (2013), "Selective Inhibition of BTK Prevents Murine Lupus and Antibody-Mediated Glomerulonephritis," *J. Immunol.*, 191(9):4540-4550.
Rellos, P. et al. (2007), "Structure and Regulation of the Human Nek2 Centrosomal Kinase," *J. Biol. Chem.*, 282(9):6833-6842.
Robak, T. & E. Robak (2012), "Tyrosine kinase inhibitors as potential drugs for B-cell lymphoid malignancies and autoimmune disorders," *Expert Opin. Investig. Drugs*, 21(7):921-947.
Sammes, M.P., et al. (1971), "α-Cyano-sulphonyl Chlorides: Their Preparation and Reactions with Amines, Alcohols, and Enamines," *J. Chem. Soc.*, I:2151-2155.
Santilli, A.A. & T.S. Osdene (1964), "8,9,10,11-Tetrahydro-12H-benzo[5,6]quinoxalino[2,3-e][1,4]diazepin-12-ones. Examples of a New Heterocyclic Ring System," *J. Org. Chem.*, 29:2066-2068.
Santus, G. & R.W. Baker (1995), "Osmotic Drug Delivery: A Review of the Patent Literature," *J. Control. Release*, 35:1-21.
Schwarz, J.B. et al. (2005), "Novel Cyclopropyl β-Amino Acid Analogues of Pregabalin and Gabapentin That Target the $α_2$-δ Protein," *J. Med. Chem.*, 48:3026-3035.
Schwöbel, J. et al. (2010), "Prediction of Michael-Type Acceptor Reactivity toward Glutathione," *Chem. Res. Toxicol.*, 23, 1576-1585.
Serafimova, I.M. et al. (2012), "Reversible targeting of noncatalytic cysteines with chemically tuned electrophiles," *Nat. Chem. Biol.*, ePub Apr. 1, 2012, 6 pages, DOI: 10.1038/nchembio.925.
Stahl, P. Heirich & C.G. Wermuth (Eds.) (2002), Handbook of Pharmaceutical Salts: Properties, Selection, and Use, Wiley-VCH; pp. 1-374.
Stevens, C.V. et al. (2002), "Synthesis of Substituted Cyclopropylphosphonates by Michael Induced Ring Closure (MIRC) Reactions," *Synlett*, 7:1089-1092.
Structure-Based Search Results (May 9, 2011, 8:13 PM), SciFinder (2 pages).
Structure-Based Search Results (May 9, 2011, 8:23 PM), SciFinder (2 pages).
Structure-Based Search Results (May 9, 2011, 8:33 PM), SciFinder (2 pages).
Structure-Based Search Results (May 9, 2011, 9:06 PM), SciFinder (2 pages).
Structure-Based Search Results (May 10, 2011, 10:04 AM), SciFinder (6 pages).
Structure-Based Search Results (May 10, 2011, 10:20 AM), SciFinder (4 pages).
Structure-Based Search Results (May 10, 2011, 10:46 AM), SciFinder (4 pages).

Verhé, R. et al. (1978), "Preparation of 2,2-Dialkylcyclopropanes Geminally Substituted with Electron-Withdrawing Groups," *Synthesis*, 7:530-532.
Verhé, R. et al. (1978), "Thermal Lactonization of Brominated Alkylidenemalonates: Synthesis of 2-Buten-4-Olides," *Bulletin des Societes Chimiques Beiges*, 87(3):215-222.
Verhé, R. et al. (1981), "Synthesis of 1,1-Bis(Hydroxymethyl) Cyclopropanes," *Org. Prep. Proced. Int.*, 13(1):13-18.
Vo, N.H. et al. (1997), "Transformations of Resin-Bound Pyridinium Ylides: I. A Stereoselective Synthesis of 2,2,3 -Trisubstituted Cyclopropanecarboxylates," *Tetrahedron Lett.*, 38(46):7951-7954.
Wang, K. et al. (2009), "Cyanoacetamide Multicomponent Reaction (I): Parallel Synthesis of Cyanoacetamides," *J. Comb. Chem.*, 11:920-927.
Wang, G.T. et al. (2010), "Substituted 4-amino-1H-pyrazolo[3,4-d]pyrimidines as multi-targeted inhibitors of insulin-like growth factor-I receptor (IGFIR) and members of ErbB-family receptor kinases," *Bioorg. Med. Chem. Lett.*, 20:6067-6071.
WebMD. 10 Ways to Prevent Psoriasis Flare-Ups. (2016) Web: <http://www.webmd.com/skin-problems-and-treatments/psoriasis/prevent-flare-ups> (8 pages).
WebMD. Multiple Sclerosis (MS)—Prevention. (2015) Web: < http://www.webmd.com/multiple-sclerosis/tc/multiple-sclerosis-ms-prevention> (4 pages).
Wells, G. et al. (2000), "Structural Studies on Bioactive Compounds. 32.[1] Oxidation of Tyrphostin Protein Tyrosine Kinase Inhibitors with Hypervalent Iodine Reagents," *J. Med. Chem.*, 43:1550-1562.
WhatisDryEye.com. Dry Eye vs. Conjunctivitis (2016) Web: <http://www.whatisdryeye.com/dry-eye-vs-conjunctivitis> (5 pages).
Wilding, I.R. et al. (1994), "Targeting of Drugs and Vaccines to the Gut," *Pharmac. Ther.*, 62:97-124.
Wissner, A. et al. (2003), "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," *J. Med. Chem.*, 46:49-63.
Xu, D. et al. (2012), "RN486, a Selective Bruton's Tyrosine Kinase Inhibitor, Abrogates Immune Hypersensitivity Responses and Arthritis in Rodents," *J. Pharm. Exp. Ther.*, 341 (1):90-103.
Zhang, F. et al. (2009), "Organic base catalyzed carbonyl allylation of methyl trifluoropyruvate with activated alkenes," *Tetrahedron*, 65:83-86.
Zimmerman, H.E. & W. Chen (2002), "The Diverted Di-π-Methane Rearrangement; Mechanistic and Exploratory Organic Photochemistry," *Org. Lett.*, 4(7): 1155-1158.
Communication Pursuant to Article 94(3) EPC for European Patent Application No. 13731218.7, dated Sep. 23, 2015 (4 pages).
English Translation of Office Action issued Apr. 12, 2013, in Chinese Application No. 201080061570.1 (2 pages).
Extended European Search Report for European Patent Application No. 17152898.7, dated Mar. 8, 2017 (7 pages).
International Preliminary Report on Patentability, dated May 22, 2012, in International Application No. PCT/US2010/056890, filed Nov. 16, 2010, by the Regents of the University of California (10 pages).
International Search Report dated Jul. 28, 2011, in International Application No. PCT/US2010/056890, filed Nov. 16, 2010, by the Regents of the University of California (7 pages).
International Search Report and Written Opinion dated Jul. 5, 2012, in International Patent Application No. PCT/US2012/038092, filed May 16, 2012, by Principia Biopharma Inc. (8 pages).
International Search Report and Written Opinion dated Aug. 20, 2012, in International Patent Application No. PCT/US2012/038120, filed May 16, 2012, by Principia Biopharma Inc. (10 pages).
International Search Report and Written Opinion dated Jul. 25, 2012, in International Application No. PCT/US2012/038135, filed May 16, 2012, by Principia Biopharma Inc. (9 pages).
International Search Report and Written Opinion dated Jul. 9, 2012, in International Patent Application No. PCT/US2012/038163, filed May 16, 2012, by Principia Biopharma Inc. (8 pages).

(56) References Cited

OTHER PUBLICATIONS

International Search Report dated Feb. 1, 2013, for International Application No. PCT/US2012/038214, filed May 16, 2012, by the Regents of the University of California et al. (5 pages).
International Search Report and Written Opinion dated Sep. 3, 2013, in International Patent Application No. PCT/US2013/045266, filed Jun. 11, 2013, by Principia Biopharma Inc. (11 pages).
International Search Report and Written Opinion dated Oct. 1, 2013, in International Patent Application No. PCT/US2013/047958, filed Jun. 26, 2013, by Principia Biopharma Inc. (14 pages).
International Search Report and Written Opinion dated Nov. 18, 2013, in International Patent Application No. PCT/US2013/053042, filed Jul. 31, 2013, by Principia Biopharma Inc. (12 pages).
International Search Report and Written Opinion dated Nov. 5, 2013, in International Patent Application No. PCT/US2013/058614, filed Sept. 6, 2013, by Principia Biopharma Inc. (11 pages).
International Search Report and Written Opinion dated Apr. 22, 2015, in International Patent Application No. PCT/US2015/016963, filed Feb. 20, 2015, by Mohammad Reza Masjedizadeh et al. (10 pages).
International Search Report and Written Opinion dated Mar. 9, 2016, in International Patent Application No. PCT/US2015/066868, filed Dec. 18, 2015, by Steven Gourlay (13 pages).
International Search Report and Written Opinion dated Apr. 18, 2016, in International Patent Application No. PCT/US2015/000515, filed Dec. 23, 2015, by Philip A. Nunn et al. (11 pages).
International Search Report and Written Opinion dated Mar. 21, 2016, in International Patent Application No. PCT/US2015/000303, filed Dec. 23, 2015, by Philip Nunn et al. (12 pages).
International Search Report and Written Opinion dated Aug. 16, 2016, in International Patent Application No. PCT/US2016/035588, filed Jun. 2, 2016, by Principia Biopharma Inc. (10 pages).
International Search Report and Written Opinion dated Oct. 6, 2016, in International Patent Application No. PCT/US2016/039070, filed Jun. 23, 2016, by Principia Biopharma Inc. (18 pages).
International Search Report and Written Opinion dated Oct. 2, 2017, in International Patent Application No. PCT/US2017/040075, filed Jun. 29, 2017, by Principia Biopharma Inc. (9 pages).
U.S. Appl. No. 15/072,244, filed Mar. 16, 2016, by Principia Biopharma Inc.
U.S. Appl. No. 15/188,941, filed Jun. 21, 2016, by Principia Biopharma Inc.

Nose fully cleared after 28 days of treatment
Pretreatment 28 days after treatment Full healing after 28 days treatment: feet pads normal (normal gait resumed within a few days)

28 days after treatment

SALTS AND SOLID FORM OF A BTK INHIBITOR

CROSS-REFERENCE TO RELATED APPLICATIONS

This application is a divisional of U.S. patent application Ser. No. 16/596,611, filed Oct. 8, 2019, which is a continuation of U.S. patent application Ser. No. 16/116,425, filed Aug. 29, 2018, now U.S. Pat. No. 10,456,403, which is a continuation of U.S. patent application Ser. No. 15/120,293, filed Aug. 19, 2016, now U.S. Pat. No. 10,092,569, which is a national phase application based on international application number PCT/US2015/016963, filed Feb. 20, 2015, and claims the benefit of provisional application Nos. 61/943,262, filed Feb. 21, 2014, 61/946,480, filed Feb. 28, 2014, and 62/096,468, filed Dec. 23, 2014, the contents of each of these applications being incorporated herein by reference.

FIELD

Disclosed herein are processes for preparing 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile free base (also referred to herein as Compound (I)) having the structure:

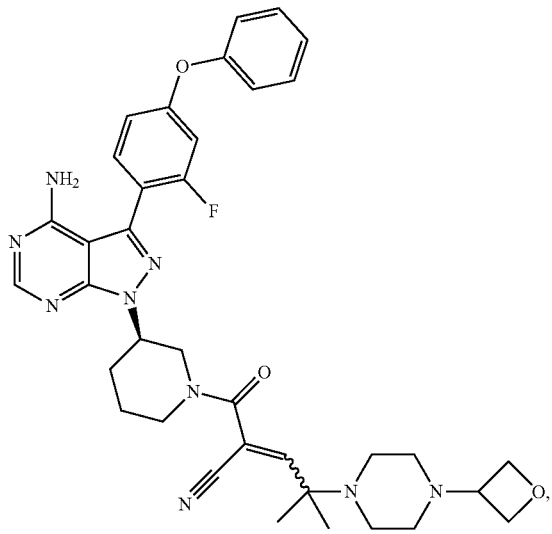 [SMILES: CC(C)(C=C(C#N)C(=O)N1CCC[C@@H](n2nc(-c3ccc(Oc4ccccc4)cc3F)c3c(N)ncnc32)C1)N1CCN(C2COC2)CC1]

(I)

certain salts of compound (I) and a solid state form of said salts. The ⁓ line at the alkene carbon, in compound (I) denotes that compound (I) or a pharmaceutically acceptable salt thereof can be E isomer, Z isomer, or a mixture of (E) and (Z) isomers. Also disclosed herein are pharmaceutical compositions comprising such salts and solid state form(s) of Compound (I) or a pharmaceutically acceptable salt thereof. Compound (I) and pharmaceutically acceptable salts thereof are potent Bruton Tyrosine Kinase (BTK) inhibitors, and hence can be useful for the treatment of diseases such as cancer, autoimmune, and inflammatory diseases.

BACKGROUND

Compound (I) is disclosed in Example 31 of the PCT Application No. PCT/US2013058614 filed on Sept. 6, 2013. The disclosed synthesis provides compound (I) requiring purification by column chromatography and affording a foam upon removal of solvent which can be crushed to obtain a powder.

For a compound to be suitable for use as a therapeutic agent, the compound synthesis must be amenable to large scale manufacturing and isolation, and the physical properties of the compound should be such that they do not negatively impact the effectiveness and cost of a formulated active ingredient.

SUMMARY

Isolation of compound (I) as described in PCT Application No. PCT/US2013058614 is less than ideal for large scale synthesis and isolation and therefore handling and formulating of the resulting compound can present challenges. In addition, when isolated as described in PCT Application No. PCT/US2013058614, the isolated compound (I) retains a higher percentage of residual solvent after drying under vacuum at ambient temperature than that allowed under the International Conference on Harmonisation of Technical Requirements for Registration of Pharmaceuticals for Human Use ("ICH") guidelines (e.g., -ICH limit for class 2 solvents ranges between 50-3880 ppm and for class 3 solvents <5000 ppm). Due to thermal instability of compound (I), further drying at elevated temperatures cannot be accomplished without the generation of compound (I) related impurities.

Additionally, in a recent pre-clinical study conducted by the Applicant in which a dog suffering from pemphigus foliaceus (PF) was administered (R,E)-2-(3-(4-amino-3-(2-fluoro-4-phenoxy-phenyl)-1H-pyrazolo[3,4-d]pyrimidin-1-yl)piperidine-1-carbonyl)-4,4-dimethylpent-2-enenitrile, a BTK inhibitor, as a single agent, it was surprisingly discovered that inhibition of BTK is effective and safe for the treatment of PF.

It was also surprisingly discovered that the manifestation of pre-clinical response with (R,E)-2-(3-(4-amino-3-(2-fluoro-4-phenoxyphenyl)-1H-pyrazolo [3,4-d]-pyrimidin-1-yl)piperidine-1-carbonyl)-4,4-dimethylpent-2-enenitrile, was as rapid and comparable to that observed with systemic corticosteroid therapy and none of the well-known corticosteroid-like adverse effects in canines, such as polyuria, polydipsia, polyphagia or weight gain, was observed.

Accordingly, among the various aspects of the present disclosure may be noted the provision of a process for the formation of compound (I) as a free flowing, processable solid, making it amenable to large scale manufacturing and isolation of compound (I). Also provided are certain pharmaceutically acceptable salts of compound (I) and a solid state form of a pharmaceutically acceptable salt of compound (I). The present disclosure also provides methods of treating a blistering disease, such as pemphigus vulgaris (PV) or pemphigus foliaceous (PF) with compound (I) or a pharmaceutically acceptable salt thereof in a mammal, use of compound (I) or a pharmaceutically acceptable salt thereof as a replacement therapy for corticosteroid therapy for diseases treatable with a corticosteroid (such as autoimmune or inflammatory disease and in particular where corticosteroids are used as first or second line therapy) where a rapid clinical response is desirable. Also, disclosed are methods of treating autoimmune and/or inflammatory diseases with compound (I) or a pharmaceutically acceptable salt thereof at a specific phase of the disease process (such as acute phase and/or at onset and duration of an acute flare) and for a limited amount of time so as to maximize short term relief, minimize long term progression of the disease, and minimize long term toxicological and other adverse effects.

Accordingly, in a first aspect disclosed herein is a sulfonic acid or a carboxylic acid salt of compound (I).

Embodiment (1a)

In one embodiment (embodiment (1a)) of the first aspect, the salt is a sulfonic acid salt of compound (I).

Within embodiment (1a), in one embodiment the sulfonic acid salt of compound (I) is mono- or di-methanesulfonic acid, mono or di-benezenesulfonic acid, mono- or di-toluenesulfonic acid, or ethane-1,2-disulfonic acid salt of compound (I). Within embodiment (1a), in another embodiment the sulfonic acid salt of compound (I) is mono- or di-methanesulfonic acid salt of compound (I). Within embodiment (1a), in yet another embodiment the sulfonic acid salt of compound (I) is di-methanesulfonic acid salt of compound (I). Within embodiment (1a), in another embodiment the sulfonic acid salt of compound (I) is mono methanesulfonic acid salt of compound (I).

Embodiment (1b)

In another embodiment (embodiment (1b)) of the first aspect, the salt is a carboxylic acid salt of compound (I).

Within embodiment (1b), in one embodiment the carboxylic acid salt of compound (I) is fumaric acid, oxalic acid, tartaric acid, maleic acid, citric acid, or malonic acid salt of compound (I).

In a second aspect, disclosed herein is an amorphous form of a pharmaceutically acceptable salt of compound (I).

Embodiment (2a)

In one embodiment (embodiment (2a)) of the second aspect, the amorphous form is of a sulfonic acid salt of compound (I).

Within embodiment (2a), in one embodiment the amorphous form is of mono- or di-methanesulfonic acid, mono or di-benezenesulfonic acid, mono- or di-toluenesulfonic acid, or ethane-1,2-disulfonic acid salt of compound (I). Within embodiment (2a), in another embodiment, the amorphous form is of mono- or di-methanesulfonic acid salt of compound (I). Within embodiment (2a), in another embodiment the sulfonic acid salt is the dimethanesulfonic acid salt of compound (I). Within embodiment (2a), in another embodiment the sulfonic acid salt is the mono methanesulfonic acid salt of compound (I).

Embodiment (2b)

In another embodiment (embodiment (2b)) of the second aspect, the amorphous form is of a carboxylic acid of compound (I).

Within embodiment (2b), in one embodiment, the amorphous form is of fumaric acid, oxalic acid, tartaric acid, maleic acid, citric acid, or malonic acid salt of compound (I).

Embodiment (2c)

In yet another embodiment (embodiment (2c)) of the second aspect, in embodiments (2a) and (2h) and embodiments contained therein, the amorphous form of any of the aforementioned salts of compound (I) is substantially free of any crystalline form(s) thereof.

Within embodiment (2c), in one embodiment, at least about 80% w/w of any of the aforementioned salts of compound (I) is in the amorphous form. Within (2c), in another embodiment at least about 85% w/w of any of the aforementioned salts of compound (I) is in the amorphous form. Within (2c), in yet another embodiment, at least about 90% w/w of any of the aforementioned salts of compound (I) is in the amorphous form. Within (2c), in yet another embodiment, at least about 95% w/w of any of the aforementioned salts of compound (I) is in the amorphous form. Within (2c), in yet another embodiment, at least about 98% w/w of any of the aforementioned salts of compound (I) is in the amorphous form. Within (2c), in yet another embodiment, at least about 99% w/w of any of the aforementioned salts of compound (I) is in the amorphous form.

Embodiment (3)

In yet another embodiment (embodiment (3)) of the first aspect, the second aspect, and embodiments contained therein (i.e., (1a), (1b), (2a), (2b), and (2c) and embodiments contained therein), the salt or amorphous form of the salt of compound (I) is a substantially pure (E) or substantially pure (Z) isomer of compound (I).

Within embodiment (3), in one embodiment at least about 80% w/w of the salt of compound (I) or the amorphous form of the salt of compound (I) is the E isomer of compound (I) or at least about 80% w/w of the salt of compound (I) or the amorphous form of the salt of compound (I) is the Z isomer of compound (I). Within embodiment (3), in another embodiment at least about 85% w/w of the salt of compound (I) or the amorphous form of the salt of compound (I) is the E isomer of compound (I) or at least about 85% w/w of the salt of compound (I) or the amorphous form of the salt of compound (I) is the Z isomer of compound (I). Within embodiment (3), in another embodiment, at least about 90% w/w of the salt of compound (I) or the amorphous form of the salt of compound (I) is the E isomer of compound (I) or at least about 90% w/w of the salt of compound (I) or the amorphous form of the salt of compound (I) is the Z isomer of compound (I). Within embodiment (3), in yet another embodiment, at least about 95% w/w of the salt of compound (I) or the amorphous form of the salt of compound (I) is the E isomer of compound (I) or at least about 95% w/w of the salt of compound (I) or the amorphous form of the salt of compound (I) is the Z isomer of compound (I). Within embodiment (3), in yet another embodiment, at least about 96% w/w of the salt of compound (I) or the amorphous form of the salt of compound (I) is the E isomer of compound (I) or at least about 96% w/w of the salt of compound (I) or the amorphous form of the salt of compound (I) is the Z isomer of compound (I). Within embodiment (3), in yet another embodiment, at least about 97% w/w of the salt of compound (I) or the amorphous form of the salt of compound (I) is the E isomer of compound (I) or at least about 97% w/w of the salt of compound (I) or the amorphous form of the salt of compound (I) is the Z isomer of compound (I). Within embodiment (3), in yet another embodiment, at least about 99% w/w of the salt of compound (I) or the amorphous form of the salt of compound (I) is the E isomer of compound (I) or at least about 99% w/w of the salt of compound (I) or the amorphous form of the salt of compound (I) is the Z isomer of compound (I). The ratio of the E to Z isomer can be calculated by methods well known in the art. One such method is HPLC total area normalization method.

In a third aspect, disclosed herein is a pharmaceutical composition comprising a therapeutically effective amount of any of the salts of compound (I) or an amorphous form of any of the salts of compound (I) disclosed in the first, the second aspect, embodiments contained in the first or second aspect (i.e., (1a), (1b,) (2a), (2b), (2c) including any embodiments disclosed therein), or embodiment (3) (including any embodiments disclosed therein), and a pharmaceutically acceptable excipient.

Embodiment (4a)

In one embodiment (embodiment (4a)) of the third aspect, the pharmaceutical composition is a solid. Within this embodiment, in one embodiment the solid formulation is a tablet, capsule or another unit dosage form suitable for oral administration to a mammal.

Embodiment (4b)

In another embodiment (embodiment (4b)) of the third aspect, the pharmaceutical composition is an emulsion.

Embodiment (4c)

In yet another embodiment (embodiment (4c)) of the third aspect, the pharmaceutical composition is a solution.

In a fourth aspect, provided is a process for making an amorphous form of compound (1) comprising:
(i) adding an isopropylacetate solution of compound (I) to an antisolvent;
(ii) removing the solvent.
In one embodiment of the fourth aspect, the antisolvent is a non-polar hydrocarbon solvent. In another embodiment of the fourth aspect, the antisolvent is heptane.

In a fifth aspect, provided is a process for making an amorphous form of a pharmaceutically acceptable salt of compound (I) comprising:
(i) adding a solution of a pharmaceutically acceptable salt of compound (I) to an antisolvent; and
(ii) removing the solvent.

Embodiment (5a)

In one embodiment (embodiment (5a)) of the fifth aspect, the amorphous form is of a sulfonic acid salt of compound (I).

Within embodiment (5a), in one embodiment, the sulfonic acid salt of compound (I) is mono- or di-methanesulfonic acid, mono or di-benezenesulfonic acid, mono- or di-toluenesulfonic acid, or ethane-1,2-disulfonic acid salt of compound (I). Within embodiment (5a), in another embodiment, the sulfonic acid salt of compound (I) is mono- or di-methanesulfonic acid salt of compound (I). Within embodiment (5a), in another embodiment the sulfonic acid salt of compound (I) is the dimethanesulfonic acid salt of compound (I). Within embodiment (5a), in another embodiment the sulfonic acid salt of compound (I) is mono methanesulfonic acid salt of compound (I).

Embodiment (5b)

In another embodiment (embodiment (5b)) of the fifth aspect, the amorphous form is of a carboxylic acid of compound (I).

Within embodiment (5b), in one embodiment the carboxylic acid salt of compound (I) is fumaric acid, oxalic acid, tartaric acid, maleic acid, or malonic salt salt of compound (I).

Embodiment (5c)

In yet another embodiment (embodiment (5c)) of the fifth aspect, in embodiment (5a) and (5b) and embodiments contained therein the amorphous form of any of the aforementioned salt of compound (I) is substantially free of any crystalline form(s) thereof.

Within (5c), at least about 80% w/w of any of the aforementioned salts of compound (I) is in the amorphous form. Within (5c), in another embodiment at least about 85% w/w of any of the aforementioned salts of compound (I) is in the amorphous form. Within (5c), in yet another embodiment, at least about 90% w/w of any of the aforementioned salts of compound (I) is in the amorphous form. Within (5c), in yet another embodiment, at least about 95% w/w of any of the aforementioned salts of compound (I) is in the amorphous form. Within (5c), in yet another embodiment, at least about 98% w/w of any of the aforementioned salts of compound (I) is in the amorphous form. Within (5c), in yet another embodiment, at least about 99% w/w of any of the aforementioned salts of compound (I) is in the amorphous form.

Embodiment 6

In yet another embodiment (embodiment (6)) of the fifth aspect and embodiments contained therein (i.e., (5a), (5b), (5c) and embodiments contained therein), the amorphous form of the salt of compound (I) is a substantially pure (E) or substantially pure (Z) isomer of compound (I).

Within embodiment 6, in one embodiment at least about 80% w/w of the salt of compound (I) or the amorphous form of the salt of compound (I) is the E isomer of compound (I) or at least about 80% w/w of the salt of compound (I) or the amorphous form of the salt of compound (I) is the Z isomer of compound (I). Within embodiment 6, in another embodiment at least about 85% w/w of the salt of compound (I) or the amorphous form of the salt of compound (I) is the E isomer of compound (I) or at least about 85% w/w of the salt of compound (I) or the amorphous form of the salt of compound (I) is the Z isomer of compound (I). Within embodiment 6, in another embodiment, at least about 90% w/w of the salt of compound (I) or the amorphous form of the salt of compound (I) is the E isomer of compound (I) or at least about 90% w/w of the salt of compound (I) or the amorphous form of the salt of compound (I) is the Z isomer of compound (I). Within embodiment 6, in yet another embodiment, at least about 95% w/w of the salt of compound (I) or the amorphous form of the salt of compound (I) is the E isomer of compound (I) or at least about 95% w/w of the salt of compound (I) or the amorphous form of the salt of compound (I) is the Z isomer of compound (I). Within embodiment 6, in yet another embodiment, at least about 96% w/w of the salt of compound (I) or the amorphous form of the salt of compound (I) is the E isomer of compound (I) or at least about 96% w/w of the salt of compound (I) or the amorphous form of the salt of compound (I) is the Z isomer of compound (I). Within embodiment 6, in yet another embodiment, at least about 97% w/w of the salt of compound (I) or the amorphous form of the salt of compound (I) is the E isomer of compound (I) or at least about 97% w/w of the salt of compound (I) or the amorphous form of the salt of compound (I) is the Z isomer of compound (I). Within embodiment 6, in yet another embodiment, at least about 99% w/w of the salt of compound (I) or the amorphous form of the salt of compound (I) is the E isomer of compound (I) or at least about 99% w/w of the salt of compound (I) or the amorphous form of the salt of compound (I) is the Z isomer of compound (I). The ratio of the E to Z isomer can be calculated by methods well know in the art. One such method is HPLC total area normalization method.

In a sixth aspect, provided is a method of treating an autoimmune disease, an inflammatory disease, or cancer in a mammal (e.g., human) in need to such treatment which method comprises administering to the mammal, a pharmaceutical composition comprising a sulfonic acid or a carboxylic acid salt of compound (I).

Embodiment (7a)

In one embodiment (embodiment (7a)) of the sixth aspect, the pharmaceutical composition comprises a sulfonic acid salt of compound (I).

Within embodiment (7a), in one embodiment, the sulfonic acid salt of compound (I) is mono- or di-methanesulfonic acid, mono or di-benezenesulfonic acid, mono- or di-toluenesulfonic acid, or ethane-1,2-disulfonic acid salt of compound (I). Within embodiment (7a), in another embodiment, the sulfonic acid salt of compound (I) is mono- or di-methanesulfonic acid salt of compound (I). Within embodiment (7a), in another embodiment the sulfonic acid of compound (I) is the dimethanesulfonic acid salt of compound (I). Within embodiment (7a), in another embodiment the sulfonic acid salt of compound (I) is mono methanesulfonic acid salt of compound (I).

Embodiment (7b)

In another embodiment (embodiment (7b)) of the sixth aspect, the pharmaceutical composition comprises a carboxylic acid salt of compound (I).

Within embodiment (7b), in one embodiment the carboxylic acid salt is fumaric acid, oxalic acid, tartaric acid, maleic acid, citric acid, or malonic acid salt of compound (I).

In a seventh aspect, provided is a method of treating a autoimmune disease, an inflammatory disease, or cancer in a mammal (e.g., human) in need to such treatment which method comprises administering to the mammal, a pharmaceutical composition comprising an amorphous form of a pharmaceutically acceptable salt of compound (I).

Embodiment (8a)

In one embodiment (embodiment (8a)) of the seventh aspect, the amorphous form is of a sulfonic acid salt of compound (I).

Within embodiment (8a), in one embodiment the amorphous form is of mono- or di-methanesulfonic acid, mono or di-benezenesulfonic acid, mono- or di-toluenesulfonic acid, or ethane-1,2-disulfonic acid salt of compound (I). Within embodiment (8a), in another embodiment, the amorphous form is of mono- or di-methanesulfonic acid salt of compound (I).

Embodiment (8b)

In another embodiment (embodiment (8b)) of the seventh aspect, the amorphous form is of is a carboxylic acid of compound (I). Within embodiment (8b), in one embodiment, the amorphous form is of fumaric acid, oxalic acid, tartaric acid, maleic acid, or malonic salt salt of compound (I).

Embodiment (8c)

In yet another embodiment (embodiment (8c)) of the seventh aspect, embodiments (8a) and (8b) and embodiments contained therein the amorphous form of any of the aforementioned salt of compound (I) is substantially free of any crystalline form(s) thereof.

Within (8c), in one embodiment, at least about 80% w/w of any of the aforementioned salts of compound (I) is in the amorphous form. Within (8c), in another embodiment at least about 85% w/w of any of the aforementioned salts of compound (I) is in the amorphous form. Within (8c), in yet another embodiment, at least about 90% w/w of any of the aforementioned salts of compound (I) is in the amorphous form. Within (8c), in yet another embodiment, at least about 95% w/w of any of the aforementioned salts of compound (I) is in the amorphous form. Within (8c), in yet another embodiment, at least about 98% w/w of any of the aforementioned salts of compound (I) is in the amorphous form. Within (8c), in yet another embodiment, at least about 99% w/w of any of the aforementioned salts of compound (I) is in the amorphous form.

Embodiment 8d

In another embodiment (embodiment (8d)) of the sixth aspect, seventh aspect, and embodiments contained therein (i.e., (7a), (7b), (8a), (8b), (8c) and embodiments contained therein), the salt of compound (I) or an amorphous form of the salt of compound (I) is a substantially pure (E) or substantially pure (Z) isomer of compound (I).

Within embodiment (8d), in one embodiment at least about 80% w/w of the salt of compound (I) or the amorphous form of the salt of compound (I) is the E isomer of compound (I) or at least about 80% w/w of the salt of compound (I) or the amorphous form of the salt of compound (I) is the Z isomer of compound (I). Within embodiment (8d), in another embodiment at least about 85% w/w of the salt of compound (I) or the amorphous form of the salt of compound (I) is the E isomer of compound (I) or at least about 85% w/w of the salt of compound (I) or the amorphous form of the salt of compound (I) is the Z isomer of compound (I). Within embodiment (8d), in another embodiment, at least about 90% w/w of the salt of compound (I) or the amorphous form of the salt of compound (I) is the E isomer of compound (I) or at least about 90% w/w of the salt of compound (I) or the amorphous form of the salt of compound (I) is the Z isomer of compound (I). Within embodiment (8d), in yet another embodiment, at least about 95% w/w of the salt of compound (I) or the amorphous form of the salt of compound (I) is the E isomer of compound (I) or at least about 95% w/w of the salt of compound (I) or the amorphous form of the salt of compound (I) is the Z isomer of compound (I). Within embodiment (8d), in yet another embodiment, at least about 96% w/w of the salt of compound (I) or the amorphous form of the salt of compound (I) is the E isomer of compound (I) or at least about 96% w/w of the salt of compound (I) or the amorphous form of the salt of compound (I) is the Z isomer of compound (I). Within embodiment (8d), in yet another embodiment, at least about 97% w/w of the salt of compound (I) or the amorphous form of the salt of compound (I) is the E isomer of compound (I) or at least about 97% w/w of the salt of compound (I) or the amorphous form of the salt of compound (I) is the Z isomer of compound (I). Within embodiment (8d), in yet another embodiment, at least about 99% w/w of the salt of compound (I) or the amorphous form of the salt of compound (I) is the E isomer of compound (I) or at least about 99% w/w of the salt of compound (I) or the amorphous form of the salt of compound (I) is the Z isomer of compound (I). The ratio of the E to Z isomer can be calculated by methods well known in the art. One such method is HPLC total area normalization method.

In one embodiment of the sixth and seventh aspects and embodiments contained therein (i.e., 7a, 7b, 8a 8b 8c, and 8d and embodiments contained therein), the mammal in need or recognized need is suffering from an autoimmune disease, e.g., thrombotic thrombocytopenic purpura, polyarteritis nodosa, cutaneous lupus, cutaneous form of systemic sclerosis(CREST), systemic sclerosis, mixed connective tissue disease, cryoglobulinemia, primary biliary sclerosis, sclerosing cholangitis, AI urticaria, IgA nephropathy, inflammatory bowel disease, such as ulcerative colitis, arthritis, lupus including Lupus Nephritis, rheumatoid arthritis, psoriatic arthritis, osteoarthritis, Still's disease, juvenile arthritis, diabetes, myasthenia gravis, granulomatosis with polyangiitis, Hashimoto's thyroiditis, Ord's thyroiditis, Graves' disease, Sjogren's syndrome, Sjogren's dry eye, non-Sjogren's dry eye disease, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, autoimmune hemolytic anemia, psoriasis, alopecia universalis, Behcet's disease, chronic fatigue, dysautonomia, endometriosis, interstitial cystitis, neuromyotonia, scleroderma, pemphigus vulgaris, and vulvodynia. In one embodiment, the disease is rheumatoid arthritis or psoriatic arthritis. In another embodiment, the autoimmune disease is lupus, pemphigus vulgaris, granulomatosis with polyangiitis, or rheumatoid arthritis.

In another embodiment of the sixth and seventh aspects and embodiments contained therein, the mammal in need or recognized need is suffering from a heteroimmune condition or disease, e.g., graft versus host disease, transplantation, transfusion, anaphylaxis, allergy, type I hypersensitivity, allergic conjunctivitis, allergic rhinitis, and atopic dermatitis.

In yet another embodiment of the sixth and seventh aspects and embodiments contained therein (i.e., 7a, 7b, 8a 8b 8c, and 8d and embodiments contained therein), the mammal in need or recognized need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis, preferably asthma or uveitis.

In yet another embodiment disclosed herein, the mammal in need or recognized need is suffering from inflammatory skin disease, such as dermatitis, contact dermatitis, eczema, urticaria, rosacea, and scarring psoriatic lesions in the skin, joints, or other tissues or organs.

In yet another embodiment of the sixth and seventh aspects and embodiments contained therein (i.e., 7a, 7b, 8a 8b 8c, and 8d and embodiments contained therein), the mammal in need or recognized need is suffering from a cancer. In one embodiment, the cancer is a B-cell proliferative disorder, e.g., diffuse large B cell lymphoma, follicular lymphoma, chronic lymphocytic lymphoma (CLL), chronic lymphocytic leukemia, chromic myleogenous leukemia, B-ALL, Philadelphia chromosome positive B-ALL,B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In yet another embodiment the sixth and seventh aspects and embodiments contained therein (i.e., 7a, 7b, 8a 8b 8c, and 8d and embodiments contained therein), the mammal in need or recognized need is suffering from a thromboembolic disorder, e.g., myocardial infarction, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

The disclosure is also directed to the sulfonic and carboxylic acid salts of compound (I) disclosed in the first aspect, an amorphous form of a pharmaceutically acceptable salt of compound (I) disclosed in the second aspect and any of the embodiments thereof disclosed above for use as a medicament. In one embodiment, the use is for treating a disease disclosed above.

The disclosure is also directed to the use of the sulfonic and carboxylic acid salts of compound (I) disclosed in the first aspect, or an amorphous form of a pharmaceutically acceptable salts of compound (I) (including the sulfonic and carboxylic acid salts of compound (I)) disclosed in the second aspect or any of the embodiments thereof disclosed above in the manufacture of a medicament for treating a disease disclosed above.

In any of the aforementioned embodiments disclosed herein involving the treatment of cancer, combination therapy can be used, i.e., the sulfonic and carboxylic acid salts of compound (I) or an amorphous form of a salt of compound (I) or any of the embodiments thereof disclosed herein can be administered in combination with at least one additional antiproliferative and/or anticancer agent. In one embodiment, the at least additional agent is chosen from alemtuzumab, arsenic trioxide, asparaginase (pegylated or non-), bevacizumab, cetuximab, platinum-based compounds, such as cisplatin, cladribine, daunorubicin/doxorubicin/idarubicin, irinotecan, fludarabine, 5-fluorouracil, gemtuzamab, methotrexate, paclitaxel, Taxol™, docetaxol, temozolomide, thioguanine, and classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, ofatumumab, hendamustine, rituximab, obinutuzumab, IPI-145, GS-1101, BKM-120, GDC-0941, DGDC-0980, GS-9820, CAL-263, Revlimid®, thalidomide®, pomalidomide®, Velcade® Kyprolis delanzomib, U0126, PD98059, PD184352, PD0325901, ARRY-142886, SB239063, SP600125, BAY 43-9006, wortmannin, Nexavar®, Tarceva®, Sutent®, Tykerb®, Sprycel®, Crizotinib, Xalkori®, or LY294002 or agents to treat signs or symptoms induced by such therapy including allopurinol, filgrastim, granisetron/ondansetron/palonosetron, dronabinol When combination therapy is used, the agents can be administered simultaneously or sequentially.

In an eighth aspect, provided is an amorphous form of mono-methanesulfonic or di-methanesulfonic salt of about 9:1 mixture of (E) isomer of compound (I), which are characterized by XRPD (X-ray Powder Diffraction) profile substantially in accordance with FIGS. 4A and 4 respectively.

In a ninth aspect, provided is a method of treating thrombotic thrombocytopenic purpura, polyarteritis nodosa, cutaneous lupus, cutaneous form of systemic sclerosis (CREST), systemic sclerosis, mixed connective tissue disease, cryoglobulinemia, primary biliary sclerosis, sclerosing cholangitis, AI urticaria, IgA nephropathy, Lupus Nephritis, autoimmune hemolytic anemia, granulomatosis with polyangiitis, or pemphigus vulgaris, in a mammal, comprising administering to said mammal a pharmaceutical composition comprising an (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds.

In one embodiment, the disease is Lupus Nephritis, autoimmune hemolytic anemia, granulomatosis with polyangiitis, or pemphigus vulgaris.

Embodiment 9

In a first embodiment (embodiment 9) of the method of the ninth aspect and embodiment contained therein, the pharmaceutical composition comprises a substantially pure (E) or (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof and the mammal is a human.

Within embodiment (9) of the ninth aspect, in a first embodiment, at least about 85% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 85% w/w of a pharmaceutically acceptable salt thereof is the (E) isomer.

Within embodiment (9), in a second embodiment, at least about 90% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 90% w/w of a pharmaceutically acceptable salt thereof is the (E) isomer.

Within embodiment (9), in a third embodiment, at least about 95% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 95% w/w of a pharmaceutically acceptable salt thereof is the (E) isomer.

Within embodiment (9) and embodiments contained therein, in one embodiment the disease is pemphigus vulgaris and the pharmaceutical composition comprising (E) isomer, (Z) isomer, a mixture of (E) and (Z) isomers, substantially pure (E) or (Z) isomers, or a mixture of (E) and (Z) isomers containing 85%, or 90%, or 95% w/w of E isomer or a mixture of (E) and (Z) isomers containing 85%, or 90%, or 95% w/w of Z isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof is optionally administered in combination with an immunosuppressive agent chosen from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-C5 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, or anti-BAFF/BlyS agent (such as belimumab, VAY736, or blisibimod), leflunomide and teriflunomide. Preferably, the pharmaceutical composition comprising (E) isomer, (Z) isomer, or a mixture of (E) and (Z) isomers, substantially pure (E) or (Z) isomer, or a mixture of (E) and (Z) isomers containing 85%, or 90%, or 95% w/w of E isomer, or a mixture of (E) and (Z) isomers containing 85%, or 90%, or 95% w/w of Z isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a pharmaceutically acceptable salt thereof is optionally administered with rituximab, ofatumumab, obinutuzumab, or veltuzumab, or a biosimilar version thereof.

In a tenth aspect, provided is a method of treating an acute inflammatory and/or autoimmune disease in a mammal in need thereof where corticosteroid therapy is used as the first or second line therapy comprising administering to said mammal in need of said treatment a therapeutically effective amount of an (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds in place of or in combination with said corticosteroid therapy; and optionally administering said (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds in combination with a noncorticosteroidal immunosupressive and/or antiinflammatory agents.

In an eleventh aspect, provided is a method of treating an inflammatory and/or autoimmune disease in a mammal in need thereof where corticosteroid therapy is used as the first or second line maintenance therapy comprising administering to said mammal in need of said treatment a therapeutically effective amount of (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]

piperidine-1-carbonyl]-4-methyl-4-[4-(oxetan-3-yl)piperazin-1-yl]pent-2-enenitrile; or a pharmaceutically acceptable salt of any of the foregoing compounds in place of or in combination with said corticosteroid therapy; and optionally administering said (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds in combination with a noncorticosteroidal immunosupressive and/or antiinflammatory agent.

In a twelfth aspect, provided is a method of eliminating or reducing a therapeutic dose of corticosteroid used in chronic maintenance therapy of an inflammatory and/or autoimmune disease in a mammal in need thereof where corticosteroid therapy is used as the first or second line comprising administering to said mammal in need of said treatment a therapeutically effective amount of (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds in place of or in combination with said corticosteroid chronic maintenance therapy; and optionally administering said (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds in combination with a noncorticosteroidal, immunosupressive, and/or antiinflammatory agents.

In a thirteenth aspect, provided is a method of treating acute flares of an autoimmune and/or inflammatory disease in a mammal in need thereof which method comprises administering to the mammal in need of said treatment a therapeutically effective amount of (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds for a treatment period sufficient to treat acute flares of the autoimmune disease. In one embodiment of the thirteenth aspect, the said (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds is used instead of corticosteroid therapy where corticosteroid therapy is normally used as the first or second line to treat flares.

Embodiment (10)

In a first embodiment (embodiment 10) of the tenth and thirteenth aspects, the acute autoimmune and/or inflammatory disease or the acute flares of an autoimmune and/or an inflammatory disease treatable by a pharmaceutical composition comprising (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile: or a pharmaceutically acceptable salt of any of the foregoing compounds, is chosen from Table (1):

TABLE (I)

| Acute indications for corticosteroid therapy | Effects of B cell therapy if known |
|---|---|
| Initial presentations or flares of rheumatic disorders such as psoriatic arthritis, rheumatoid arthritis, ankylosing spondylitis, bursitis, tenosynovitis, gout, synovitis of osteoarthritis, epicondylitis | Rituximab takes 4-12 weeks to take effect in rheumatoid arthritis (ref Rituxan US label) |
| Initial presentation or flares of collagen disease such as systemic lupus erythematosus (SLE), dermato/polymyositis, rheumatic carditis, vasculitis | Rituximab has delayed effect in ANCA-associated vasculitis and achieves remission in only 64% of cases despite concomitant use of corticosteroids for 5 months (Stone et al. 2010). Belimumab, an anti-Blys antibody, has a modest and delayed effect on improvement of chronic SLE including the ability to reduce corticosteroid use to <7.5 mg of prednisone at week 40-52 in no more than 21% of patients (Benlysta US Product Information). |
| Initial presentations or flares of dermatologic diseases such as pemphigus, Stevens-Johnson syndrome, exfoliative dermatitis, mycosis fungoides, severe psoriasis, severe seborrheic dermatitis | Rituximab has delayed effect in pemphigus vulgaris with maximal effect at 8-12 weeks (Lundardon & Payne 2012) |
| Control of incapacitating allergic reactions including asthma, contact or atopic dermatitis, serum sickness, drug hypersensitivity | |
| Initial presentations or flares of ophthalmic diseases including allergic corneal ulcers, herpes zoster of the eye, anterior or posterior inflammation/uveitis or choroiditis, sympathetic ophthalmia, allergic conjunctivitis, keratitis, chorioretinitis, optic neuritis, iritis, iridocyclitis | |
| Initial presentations or flares of respiratory | |

TABLE (I)-continued

| Acute indications for corticosteroid therapy | Effects of B cell therapy if known |
|---|---|
| diseases including symptomatic sarcoidosis, Loeffler's syndrome, berylliosis, fulminating or disseminated tuberculosis, aspiration pneumonitis | |
| Initial presentations or flares of hematologic disorders including idiopathic thrombocytopenic purpura, secondary thrombocytopenia, autoimmune hemolytic anemia, erythroblastopenia, congenital hypoplastic anemia | |
| Acute nephrotic syndrome of SLE | |
| Initial presentations or flares of gastrointestinal disease such as ulcerative colitis, Crohn's disease | |
| Acute neurological trauma to reduce swelling | |

Embodiment (11)

In an embodiment (embodiment 11) of the tenth, eleventh, twelfth, and thirteenth aspects, the autoimmune and/or inflammatory disease is chosen from indications where Prednisone is used as a therapeutic agent (see product label). Prednisone Tablets and Solutions are Indicated in the Following Conditions:

Endocrine Disorders: Primary or secondary adrenocortical insufficiency (hydrocortisone or cortisone is the first choice: synthetic analogs may be used in conjunction with mineralocorticoids where applicable; in infancy mineralocorticoid supplementation is of particular importance); congenital adrenal hyperplasia; nonsuppurative thyroiditis; hypercalcemia associated with cancer.

Rheumatic Disorders: As adjunctive therapy for short-term administration (to tide the patient over an acute episode or exacerbation) in: psoriatic arthritis, rheumatoid arthritis, including juvenile rheumatoid arthritis (selected cases may require low-dose maintenance therapy), ankylosing spondylitis, acute and subacute bursitis, acute nonspecific tenosynovitis, acute gouty arthritis, post-traumatic osteoarthritis, synovitis of osteoarthritis, epicondylitis.

Collagen Diseases: During an exacerbation or as maintenance therapy in selected cases of: systemic lupus erythematosus, systemic dermatomyositis (polymyositis), acute rheumatic carditis.

Dermatologic Diseases: Pemphigus; bullous dermatitis herpetiformis; severe erythema multiforme (Stevens-Johnson syndrome); exfoliative dermatitis; mycosis fungoides; severe psoriasis; severe seborrheic dermatitis.

Allergic States: Control of severe or incapacitating allergic conditions intractable to adequate trials of conventional treatment: seasonal or perennial allergic rhinitis; bronchial asthma; contact dermatitis; atopic dermatitis; serum sickness; drug hypersensitivity reactions.

Ophthalmic Diseases: Severe acute and chronic allergic and inflammatory processes involving the eye and its adnexa such as: allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis.

Respiratory Diseases: Symptomatic sarcoidosis; Loeffler's syndrome not manageable by other means; berylliosis; aspiration pneumonitis, fulminating or disseminated pulmonary tuberculosis when used concurrently with appropriate antituberculous chemotherapy Hematologic Disorders: Idiopathic thrombocytopenic purpura in adults; secondary thrombocytopenia in adults; acquired (autoimmune) hemolytic anemia; erythroblastopenia (RBC anemia); congenital (erythroid) hypoplastic anemia.

Neoplastic Diseases: For palliative management of: leukemias and lymphomas in adults, acute leukemia of childhood.

Edematous States: To induce a diuresis or remission of proteinuria in the nephrotic syndrome, without uremia, of the idiopathic type or that due to lupus erythematosus.

Gastrointestinal Diseases: To tide the patient over a critical period of the disease in: ulcerative colitis, regional enteritis.

Miscellaneous: Tuberculous meningitis with subarachnoid block or impending block when used concurrently with appropriate antituberculous chemotherapy; trichinosis with neurologic or myocardial involvement.

Embodiment (12)

In a second embodiment (embodiment 12) of the tenth, eleventh, twelfth, and thirteenth aspects, the disease is pemphigus vulgaris (PV) or pemphigus foliaceus (PF).

Embodiment (13)

In a third embodiment (embodiment 13) of the tenth, eleventh, twelfth, and thirteenth aspects, and embodiments (10), (11), and (12) contained therein, the (E) isomer, (Z) isomer, or a mixture of (E) and (Z) isomer of 2-[(3R)-3-[4-amino-3-(2-fluoro-4-phenoxy-phenyppyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds is administered as a monotherapy.

Embodiment (14)

In a fourth embodiment (embodiment 14) of the tenth, eleventh, twelfth, and thirteenth aspects, and embodiments (10), (11), and (12) contained therein, the (F) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan- 3-yl)piperazin-1-yl]pent-2-enenitrile; or a pharmaceutically acceptable salt of any of the foregoing compounds is administered in acute PV or acute PF in place of or in combination with cortisterods and optionally in combination with an immunosuppressive agent chosen from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as ahatacept or belatacept, anti-sphingosine-1-phosphate receptor agent such as fingolimod, anti-C5 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, or anti-BAFF/BlyS agent (such as belimumab, VAY736, or blisibimod), leflunomide and teriflunomide. Preferably, the immunosuppressive agent is rituximab, ofatumumab, obinutuzumab, or veltuzumab, or a biosimilar version thereof.

Embodiment (15)

In a fifteenth embodiment (embodiment 15) of the tenth, eleventh, twelfth, and thirteenth aspects, and embodiments (10), (11), and (12) contained therein, the (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds is administered in acute pemphigus vulgaris or acute pemphigus foliaceus in place of corticosteroids and administered optionally in combinations with an immunosuppressive agent chosen from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimwnab, or certolizumab pegol or a biosimilar version thereof), anti-IL6 agent toward ligand or its receptors (such as tocilizumab, sarilumab, olokizurnab, elsililurnab, or siltuximab), anti-IL17 agent to ligand or its receptors (such as secukinumab, ustekinumab, brodalumab, or ixekizurnab), anti-IL1 agent to ligand or its receptors (such as with rilonacept, canakinurnab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-C5 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, or anti-BAFF/BlyS agent (such as belimumab, VAY736, or blisihimod), leflunomide and teriflunomide. Preferably, the immunosuppressive agent is rituximab, ofatumumab, obinutuzumab, or veltuzumab, or a biosimilar version thereof.

In yet another embodiment of any of the above aspects, the compound disclosed herein is injected locally into the patient to treat the condition of small areas of the body. Examples of conditions for which local injections can be used include inflammation of a bursa (bursitis of the hip, knee, elbow, or shoulder), a tendon (tendinitis, such as tennis elbow), and a joint (arthritis). Knee osteoarthritis, hip bursitis, painful foot conditions such as plantar fasciitis, and rotator cuff tendinitis may be treated by local injection of a compound of present disclosure. In a fourteenth aspect, provided is a method of treating an autoimmune disease and/or inflammatory disease in a mammal which method comprises administering to the mammal in need thereof a therapeutically effective amount of (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt in combination with an immunosuppressive agent having slow manifestions of clinical effect.

In one embodiment of the fourteenth aspect, the immunosuppressive agent is a biologic chosen from as interferon alpha, interferon gamma, an anti-CD20 agent (such as rituximab, ofatumurnab, obinutuzumab, veltuzumab, or a biosimilar version thereof), anti-TNFalpha agent (such as entanercept, infliximab, golilumab, adalimumab, certolizumab pegol or a biosimilar version thereof), anti-11,6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors such as with basiliximab or daclizumab, anti-CD2 agent such as alefacept, anti-CD3 agent such as muromonab-cd3, anti-CD80/86 agent such as with abatacept orbelatacept, anti-C5 agent such as eculizumab, anti-integrin alpha4 agent such as natalizumab, anti-$\alpha_4\beta_7$ agent such as vedolizumab, and anti-BAFF/BlyS agent (such as belimunab, VAY736, or blisibimod). Preferably, the immunosuppressive agent is rituximab, ofatumumab, obinutuzumab, or veltuzumab, or a biosimilar version thereof.

Representative advantages of the above methods, include sparing the patient of disease activity without irnmunosuppression for prolonged periods that can lead to serious side effects. Additionally, the longer the acute flares and acute phases persist the more likely the disease process will progress and cause serious complications. Thus prompt remission of acute phases and acute flares will have a beneficial effect on the course of the disease, even without continued administration or maintenance of the active agents.

Embodiment (16)

In any of the tenth, eleventh, twelfth, thirteenth and fourteenth apects, embodiment (10), (11), (12), (13), (14) and (15), and embodiments contained therein the mammal is administered a therapeutically effective amount of a substantially pure (E) or (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt thereof. Within embodiment (16), in a first embodiment, at least about 85% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 85% w/w of a pharmaceutically acceptable salt thereof is the (E) isomer. Within embodiment (16), in a second embodiment, at least about 90% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 90% w/w of a pharmaceutically acceptable salt thereof is the (E) isomer. Within embodiment (16), in a third embodiment, at least about 95% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 95% w/w of a pharmaceutically acceptable salt thereof is the (E) isomer. Within embodiment (16), in a fourth embodiment, at least about 85% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 85% w/w of a pharmaceutically acceptable salt thereof is the (Z) isomer. Within embodiment (16), in a fifth embodiment, at least about 90% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or at least about 90% w/w of a pharmaceutically acceptable salt thereof is the (Z) isomer. Within embodiment (16), in a sixth embodiment, at least about 95% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yppiperazin-1-yl]pent-2-enenitrile; or at least about 95% w/w of a pharmaceutically acceptable salt thereof is the (Z) isomer.

Within embodiment (16), and embodiments one to six contained therein, in one embodiment 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile is present as a free base or as a sulfonic (such as mesylate) or carboxylic acid salt. Within embodiment (16), and embodiments one to sixth contained therein, in another embodiment 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or a sulfonic (such as mesylate) or carboxylic acid salt thereof is in amorphous form.

The present disclosure also included Embodiments 20-55 below:

20. A sulthnic acid or carboxylic acid salt of compound (I):

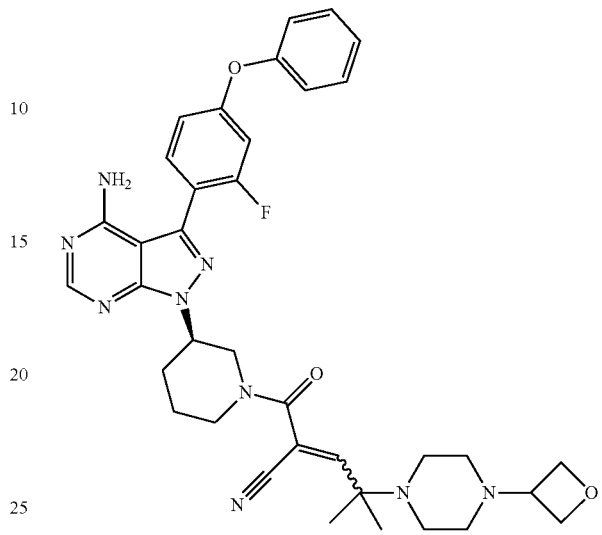

(I)

21. The sulfonic acid or carboxylic acid salt of compound (I) of embodiment 20 wherein the salt is a sulfonic acid salt.

22. The sulfonic acid salt of compound (I) of embodiment 21 wherein the sulfonic acid salt is mono- or di-methanesulfonic acid, mono or di-benezenesulfonic acid, mono- or di-toluenesulfonic acid, or ethane-1,2-disulfonic acid salt.

23. The sulfonic acid salt of compound (I) of embodiment 22 wherein the sulfonic salt is mono- or di-methanesulfonic acid salt.

24. The sulfonic acid or carboxylic acid salt of compound (I) of embodiment 20 wherein the salt is a carboxylic acid salt.

25. An amorphous form of a pharmaceutically acceptable salt of compound (I)

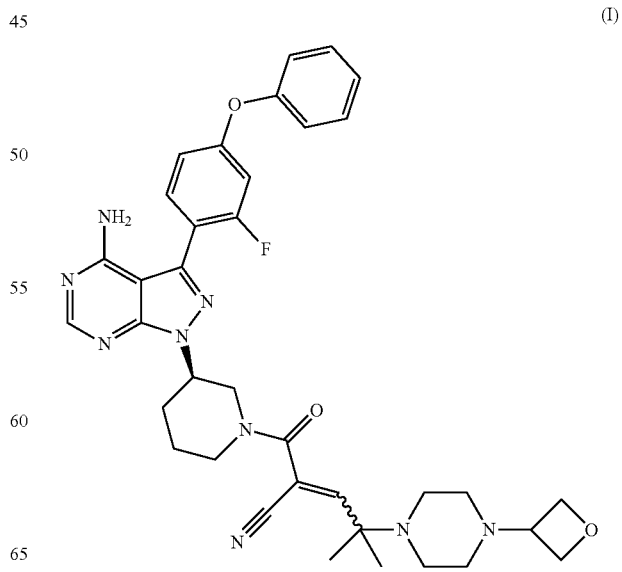

(I)

26. The amorphous form of a pharmaceutically acceptable salt of compound (I) of embodiment 25 wherein the pharmaceutically acceptable salt is a sulfonic acid or a carboxylic acid salt.

27. The amorphous form of a pharmaceutically acceptable salt of compound (I) of embodiment 26 wherein the pharmaceutically acceptable salt is a sulfonic acid salt.

28. The amorphous form of a pharmaceutically acceptable salt of compound (I) of embodiment 27 wherein the sulfonic acid salt is mono- or di-methanesulfonic acid, mono or di-benezenesulfonic acid, mono- or di-toluenesulfonic acid, or ethane-1,2-disulfonic acid salt.

29. The amorphous form of a pharmaceutically acceptable salt of compound (I) of embodiment 27 wherein the sulfonic salt is mono- or di-methanesulfonic acid salt.

30. The amorphous form of a pharmaceutically acceptable salt of compound (I) of embodiment 26 wherein the pharmaceutically acceptable salt is a carboxylic acid salt.

31. The amorphous form of a pharmaceutically acceptable salt of compound (I) of any of the embodiments 25-30 wherein the amorphous form is substantially free of any crystalline form(s) of the pharmaceutically acceptable salt of compound (I).

32. The amorphous form of a pharmaceutically acceptable salt of compound (I) of any of the embodiments 25-30 wherein at least about 80% w/w of the pharmaceutically acceptable salt of compound (I) is in amorphous form.

33. The amorphous form of a pharmaceutically acceptable salt of compound (I) of any of the embodiments 25-30 wherein at least about 90% w/w of the pharmaceutically acceptable salt of compound (I) is in amorphous form.

34. The amorphous form of a pharmaceutically acceptable salt of compound (I) of any of the embodiments 25-30 wherein at least about 99% w/w of the pharmaceutically acceptable salt of compound (I) is in amorphous form.

35. The sulfonic acid or carboxylic acid salt of compound (I) of any of the embodiments 20-24 wherein the salt of compound (I) is a substantially pure E or Z isomer.

36. The amorphous form of a pharmaceutically acceptable salt of compound (I) of any of the embodiments 25-34 wherein the salt of compound (I) is a substantially pure E or Z isomer.

37. The sulfonic acid or carboxylic acid salt of compound (I) of embodiment 35 wherein at least about 80% w/w of the salt of compound (I) is the E isomer.

38. The sulfonic acid or carboxylic acid salt of compound (I) of embodiment 35 wherein at least about 90% w/w of the salt of compound (I) is the E isomer.

39. The sulfonic acid or carboxylic acid salt of compound (I) of embodiment 35 wherein at least about 95% w/w of the salt of compound (I) is the E isomer.

40. The sulfonic acid or carboxylic acid salt of compound (I) of embodiment 35 wherein at least about 80% w/w of the salt of compound (I) is the Z isomer.

41. The sulfonic acid or carboxylic acid salt of compound (I) of embodiment 35 wherein at least about 90% w/w of the salt of compound (I) is the Z isomer.

42. The sulfonic acid or carboxylic acid salt of compound (I) of embodiment 35 wherein at least about 95% w/w of the salt of compound (I) is the Z isomer.

43. The amorphous form of a pharmaceutically acceptable salt of compound (I) of embodiment 36 wherein at least about 80% w/w of the pharmaceutically acceptable salt of compound (I) is the F isomer.

44. The amorphous form of a pharmaceutically acceptable salt of compound (I) of embodiment 36 wherein at least about 90% w/w of the pharmaceutically acceptable salt of compound (I) is the E isomer.

45. The amorphous form of a pharmaceutically acceptable salt of compound (I) of embodiment 36 wherein at least about 95% w/w of the pharmaceutically acceptable salt of compound (I) is the E isomer.

46. The amorphous form of a pharmaceutically acceptable salt of compound (I) of embodiment 36 wherein at least about 80% w/w of the pharmaceutically acceptable salt of compound (I) is the Z isomer.

47. The amorphous form of a pharmaceutically acceptable salt of compound (I) of embodiment 36 wherein at least about 90% w/w of the pharmaceutically acceptable salt of compound (I) is the Z isomer.

48. The amorphous form of a pharmaceutically acceptable salt of compound (I) of embodiment 36 wherein at least about 95% why of the pharmaceutically acceptable salt of compound (I) is the Z isomer.

49. An amorphous form of mono- or dimesylate salt of compound (I) or a substantially pure (E) or (Z) isomer thereof having XRPD substantially as in FIG. 4A and FIG. 4 respectively.

50. A pharmaceutical composition comprising the sulfonic acid or carboxylic acid salt of compound (I) of any of the embodiments 20-24, 35, and 37-42 or the amorphous form of a pharmaceutically acceptable salt of compound (I) of any of the embodiments 25-34, 36, and 43-48.

51. A method of treating a autoimmune disease, an inflammatory disease, or cancer in a mammal in need of such treatment which method comprises administering to the mammal, a pharmaceutical composition of embodiment 50.

52. The method of embodiment 51 wherein the mammal is a human in need of such treatment.

53. The method of embodiment 51 or 52 wherein the autoimmune disease is lupus, phemphigus vulgaris, granulomatosis with polyangiitis, or rheumatoid arthritis.

54. A method of treating lupus nephritis, autoimmune hemolytic anemia, granulomatosis with polyangiitis, or pemphigus vulgaris in a mammal, comprising administering to said mammal a pharmaceutical composition comprising:

an (E) isomer, (Z) isomer, or a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or a pharmaceutically acceptable salt of any of the foregoing compounds.

55. The method embodiment 54 wherein the pharmaceutical composition comprises a substantially pure (E) or (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, or a pharmaceutically acceptable salt thereof and the mammal is a human.

BRIEF DESCRIPTION OF THE FIGURES

A representative HPLC trace of compound (I) prepared according to Example 1 representing separation of the E and Z isomers of compound (I) prepared according to Example 1 is shown in FIG. 1A below A representative XRPD diffractogram of an amorphous form of compound (I) having an E/Z ratio of about 9/1, prepared according to Example 1, is shown in FIG. 1B below.

A representative XRPD diffractogram for hemi-H₂SO₄ salt of compound (I) having an E/Z ratio of about 9/1 prepared according to Example 2 is shown in FIG. 2A below.

Figure 1A:
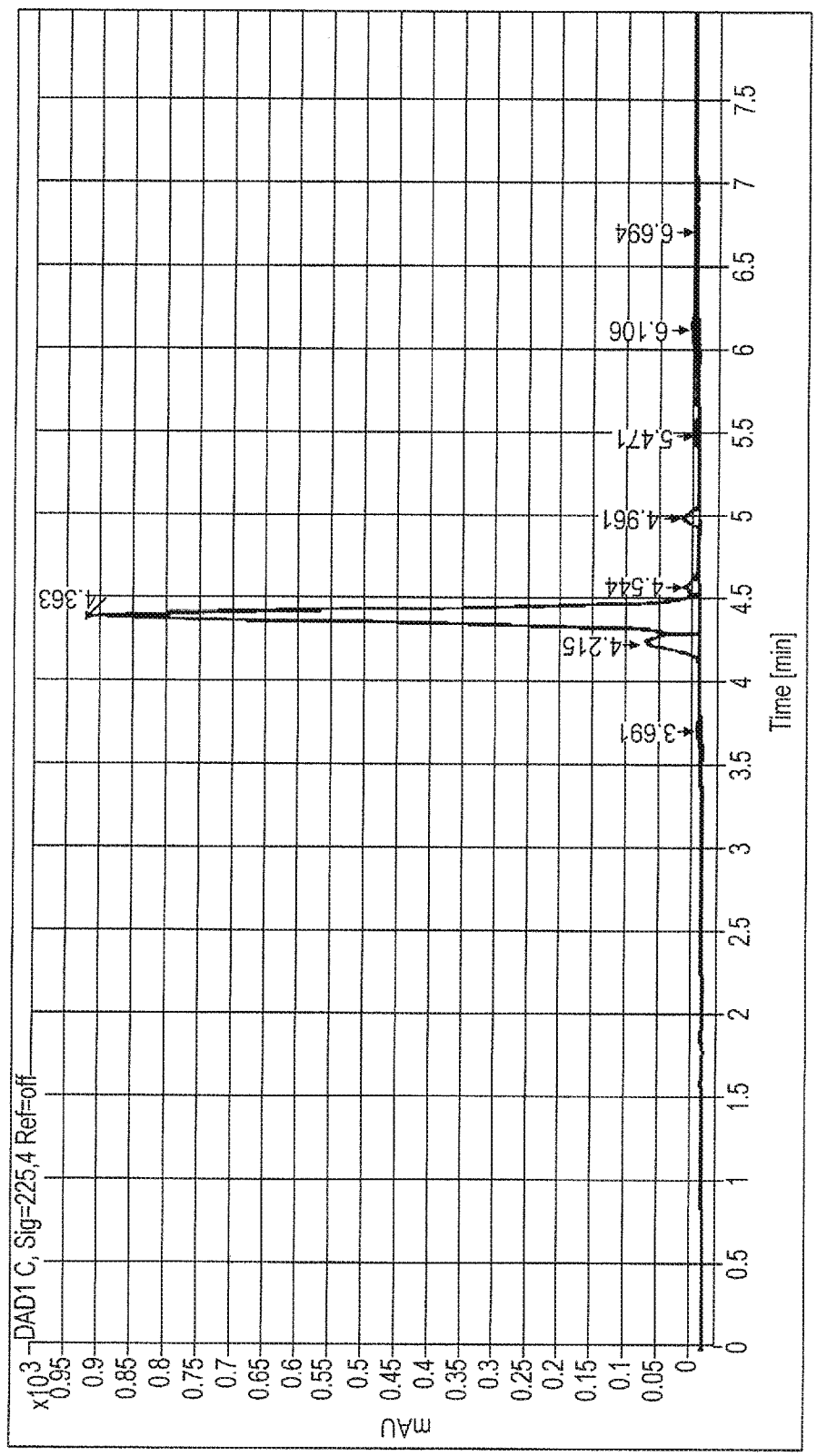
Figure 1B:
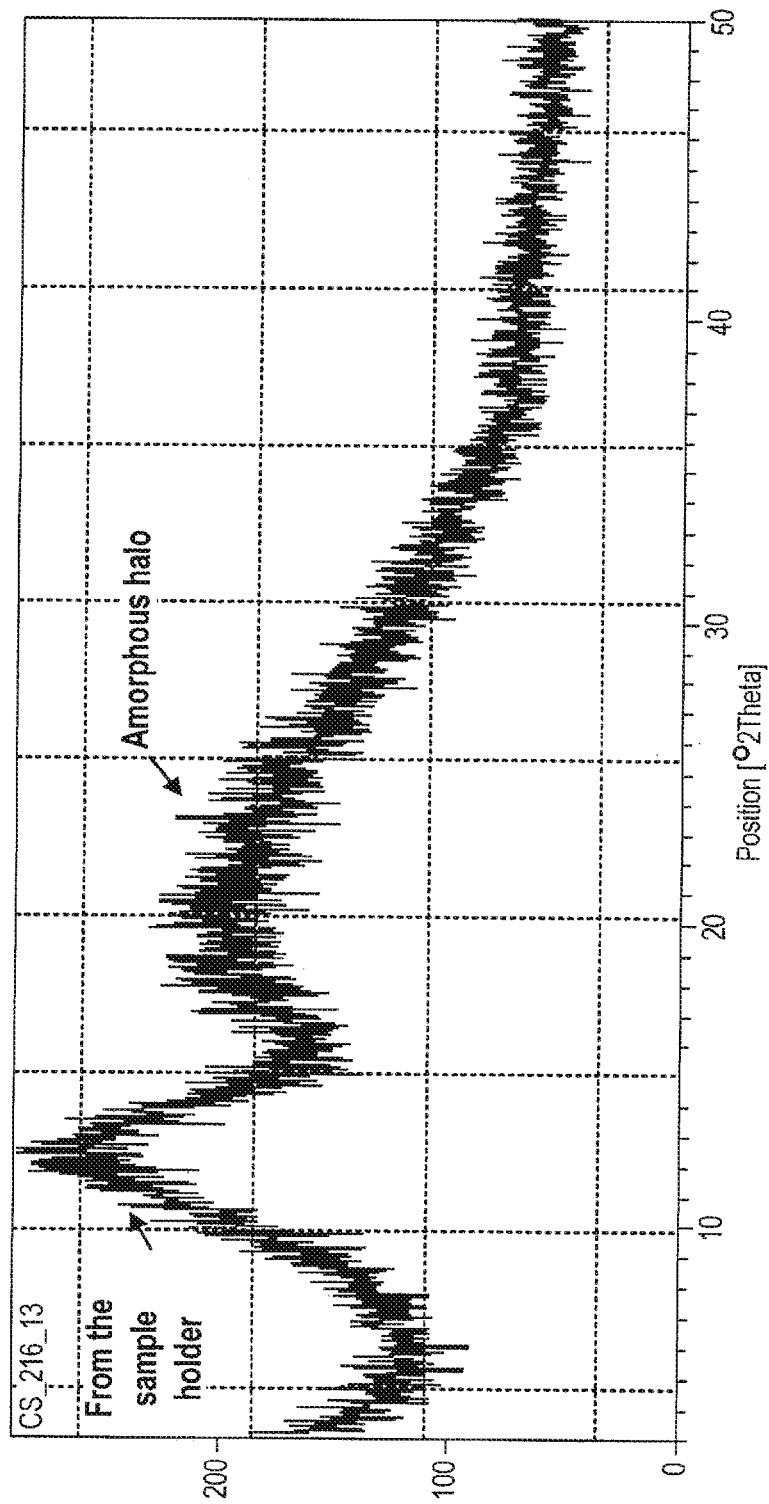
Figure 2A:
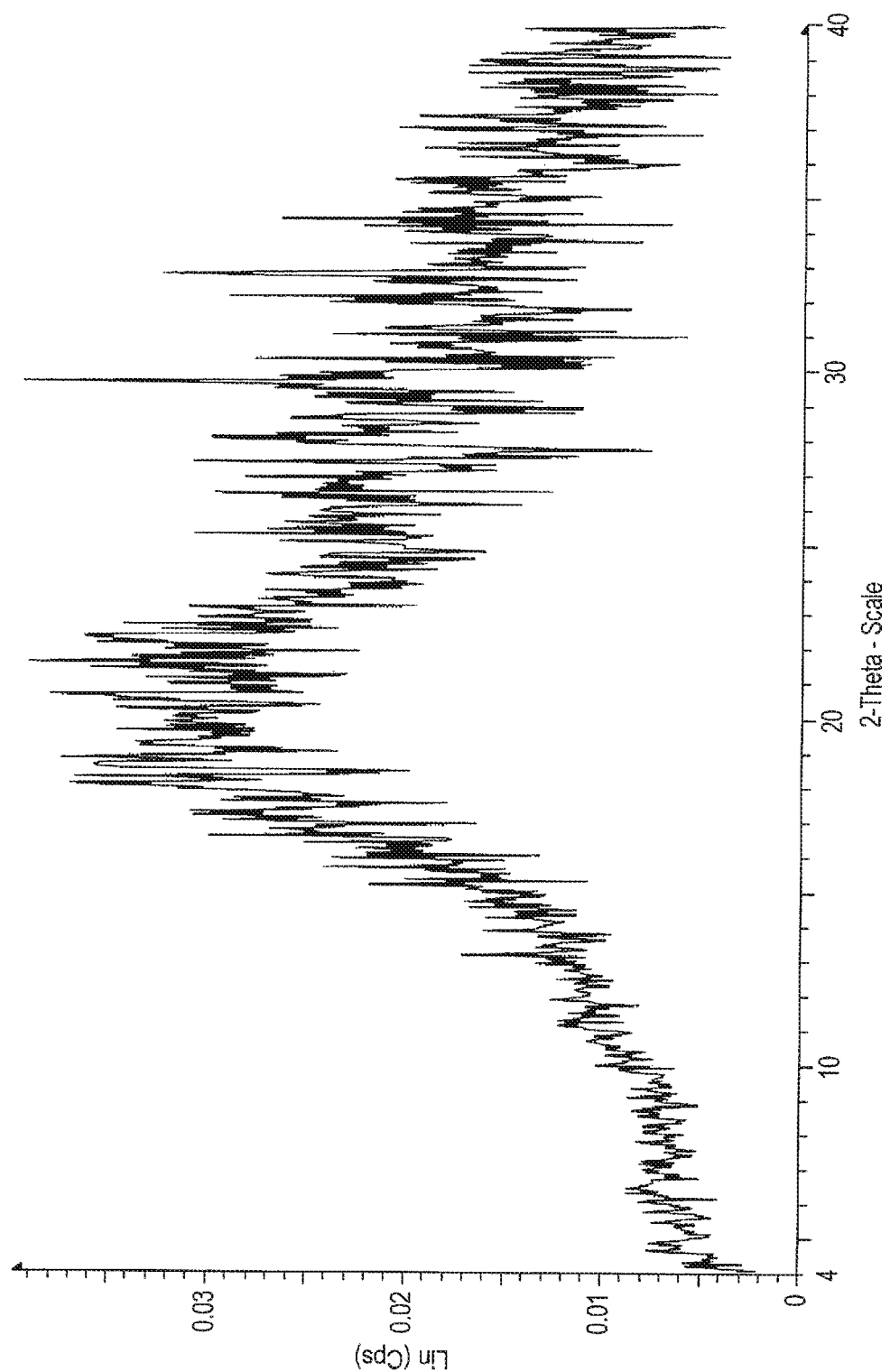
Figure 2B:
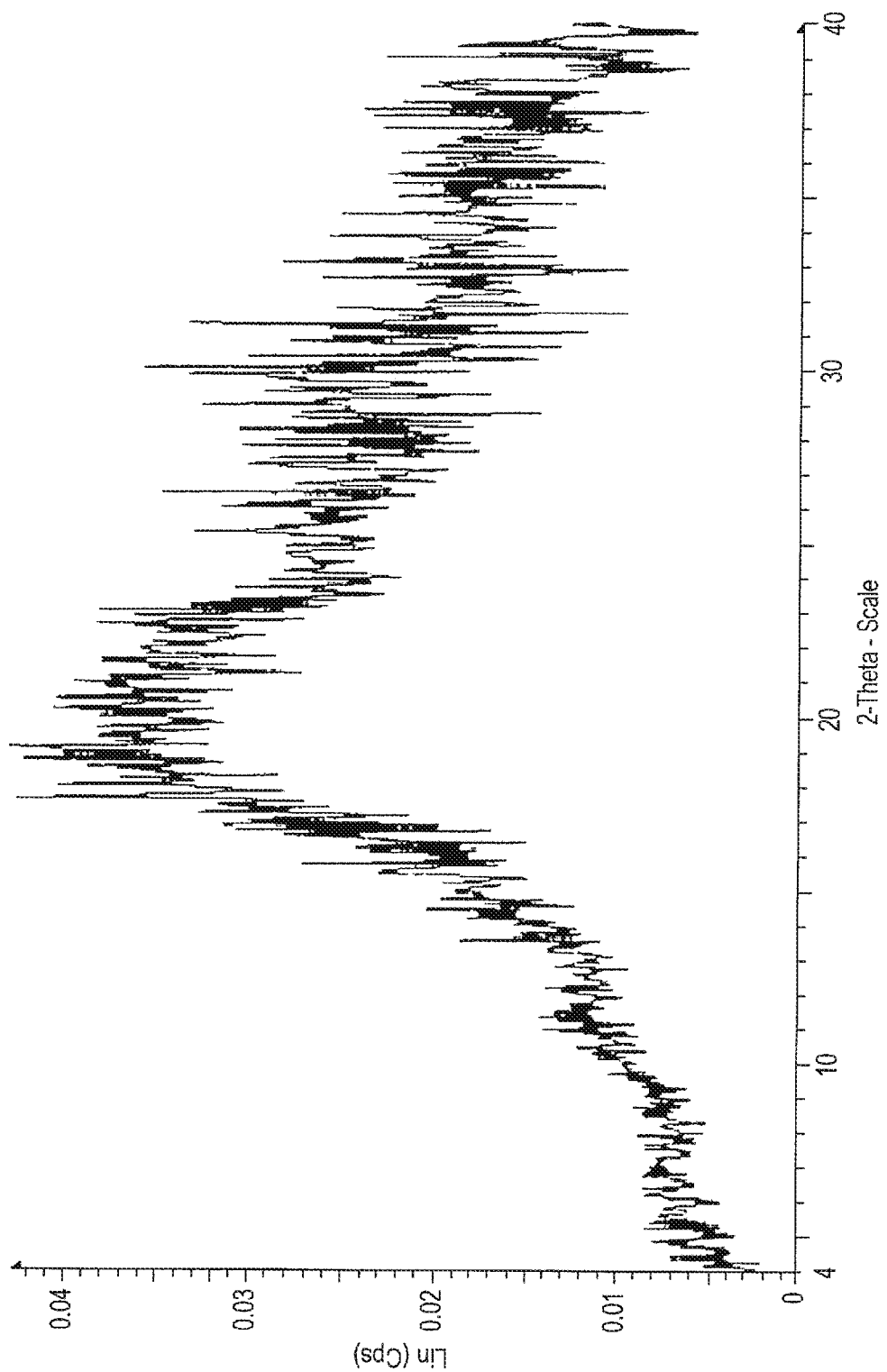

A representative XRPD diffractogram for H₂SO₄ salt from ethylacetate of compound (I) having an E/Z ratio of about 9/1 prepared according to Example 2 is shown in FIG. 2B below.

Figure 3:
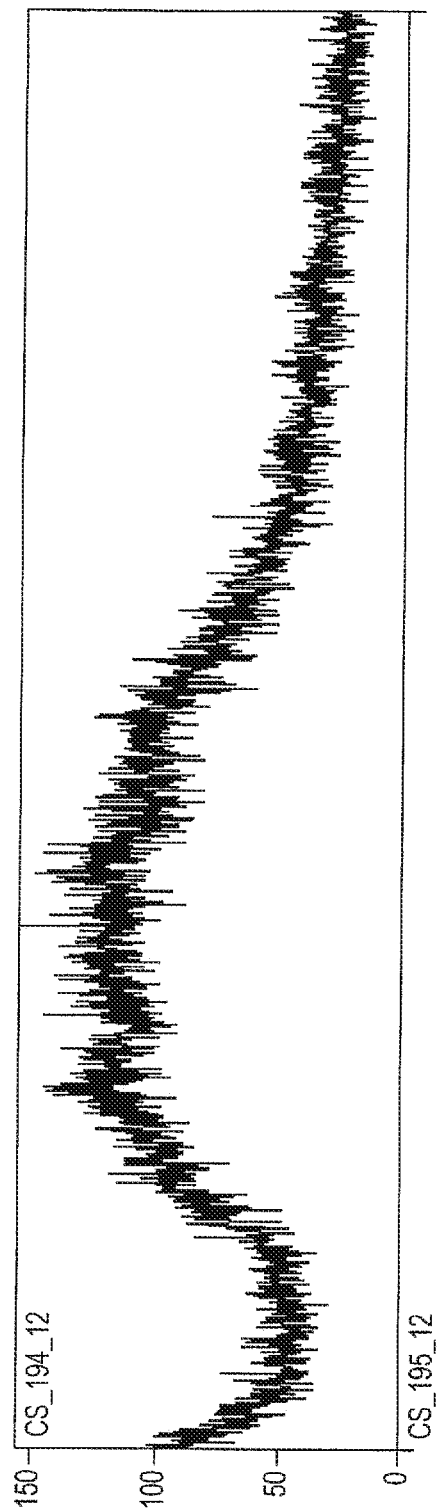

A representative XRPD diffractogram of an amorphous form of mono-HCl salt of compound (I) having an E/Z ratio of about 9/1 prepared according to Example 3 is shown in FIG. 3 below.

Figure 3A:
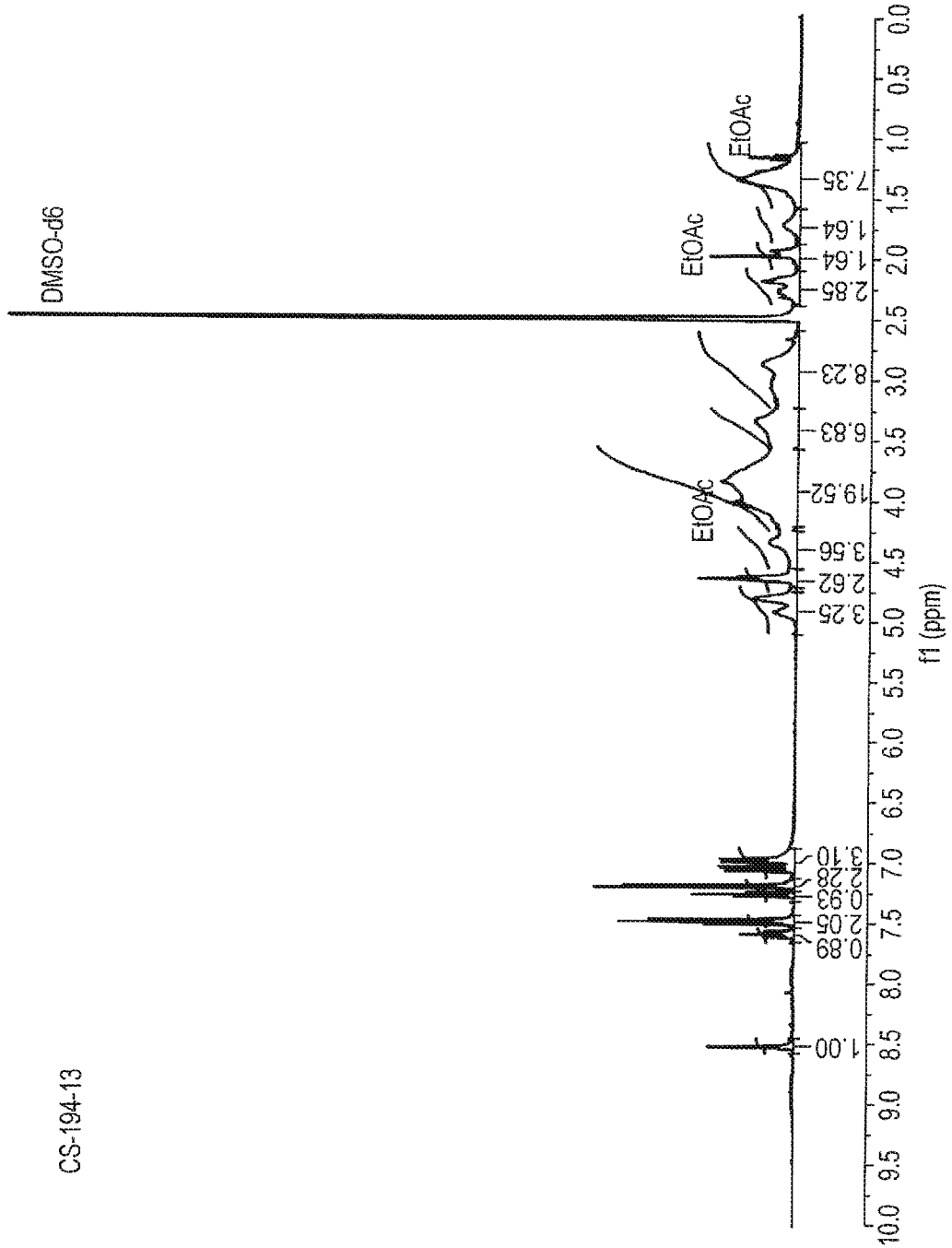

A representative ¹HNMR spectrum of mono-HCl salt having an E/Z ratio of about 9/1 prepared in DMSO-d6 according to Example 3 is shown in FIG. 3A.

Figure 4:
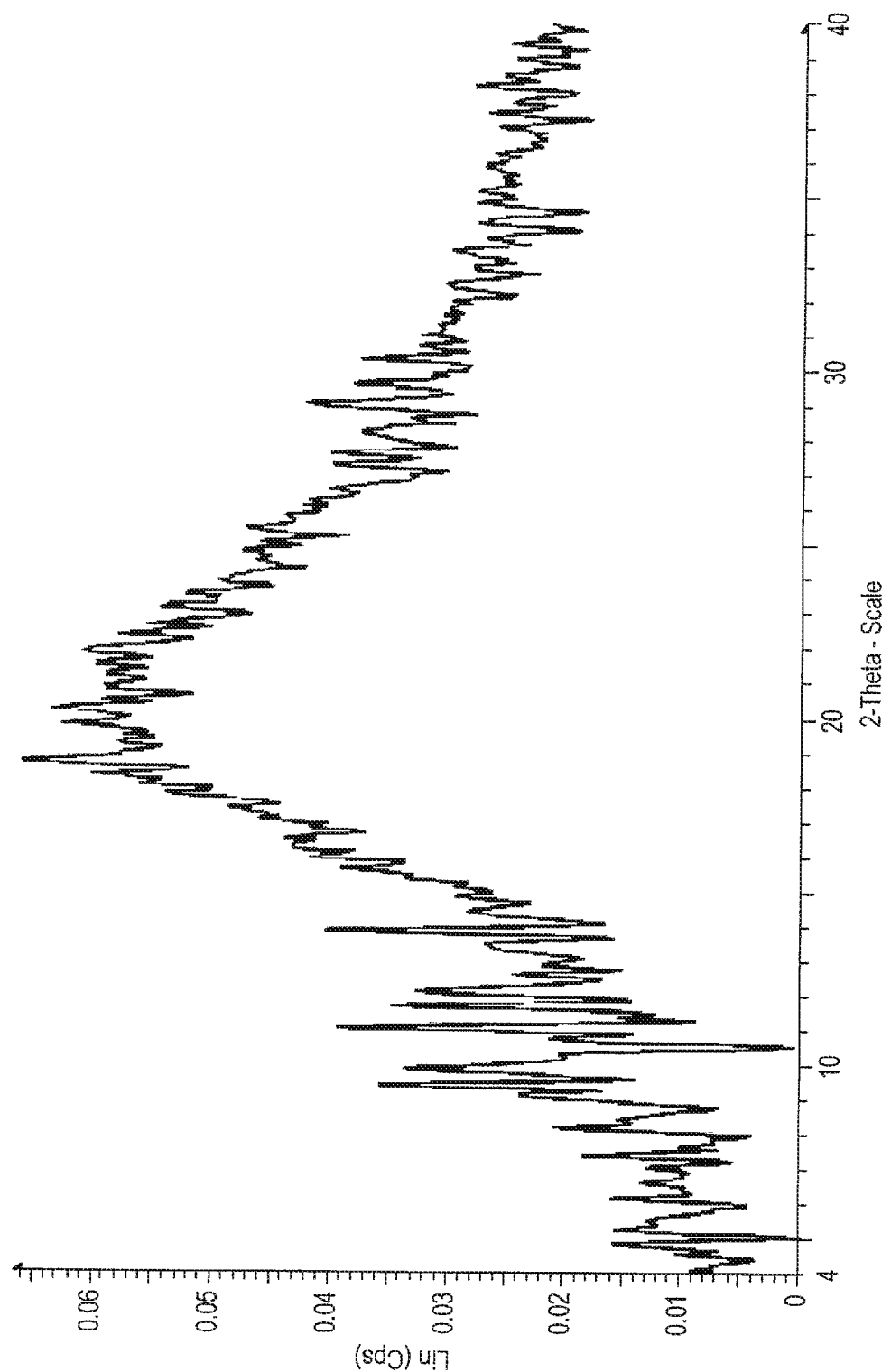
Figure 4A:
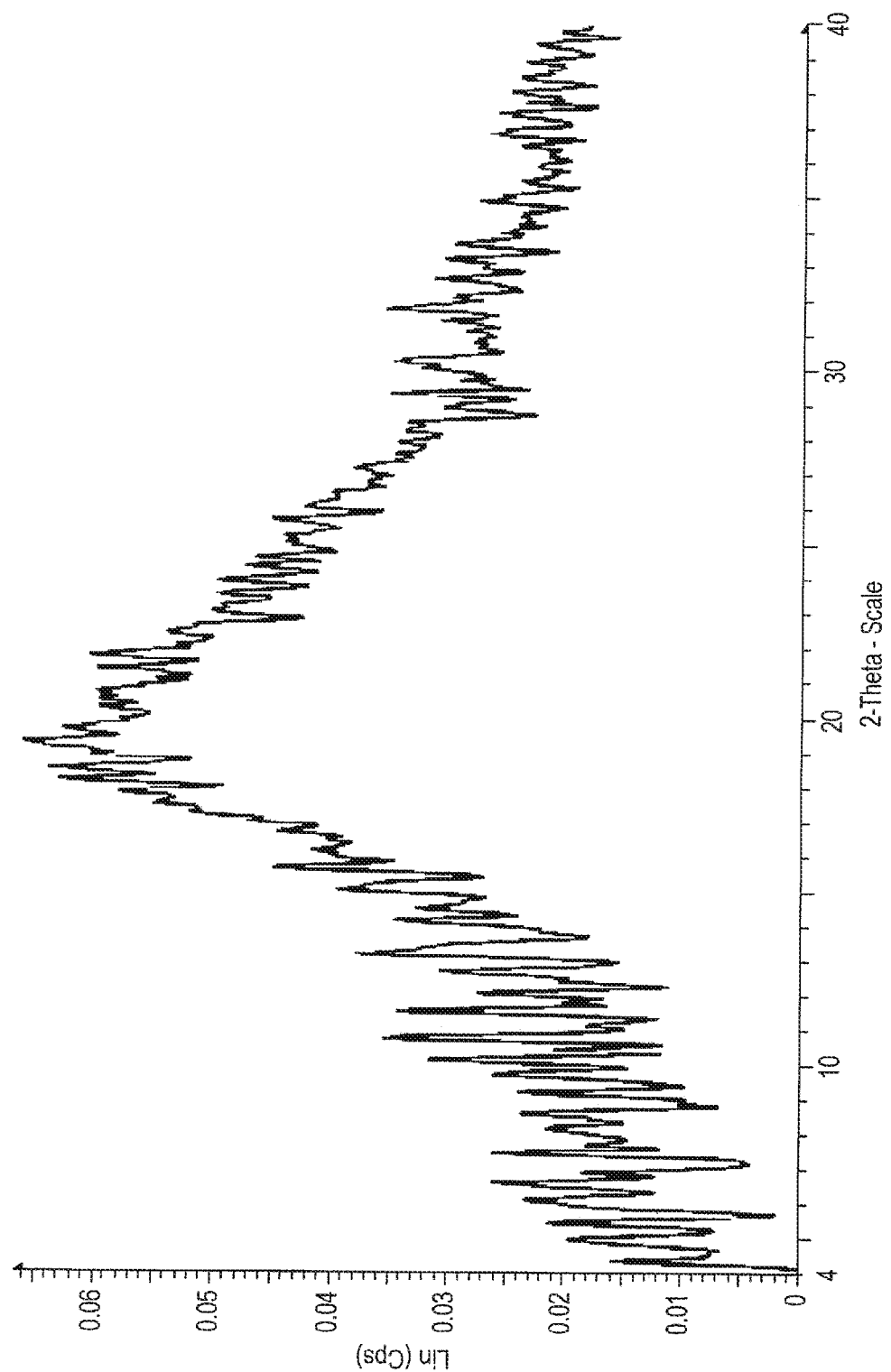

A representative XRPD diffractogram for mono-methanesulfonic acid salt of compound (I) having an E/Z ratio of about 9/1 prepared in MTBE according to Example 4 is shown in FIG. 4A.

A representative XRPD diffractogram for di-methanesulfonic salt of compound (I) having an E/Z ratio of about 9/1 prepared in MTBE according to Example 4 is shown in FIG. 4.

Figure 4B:
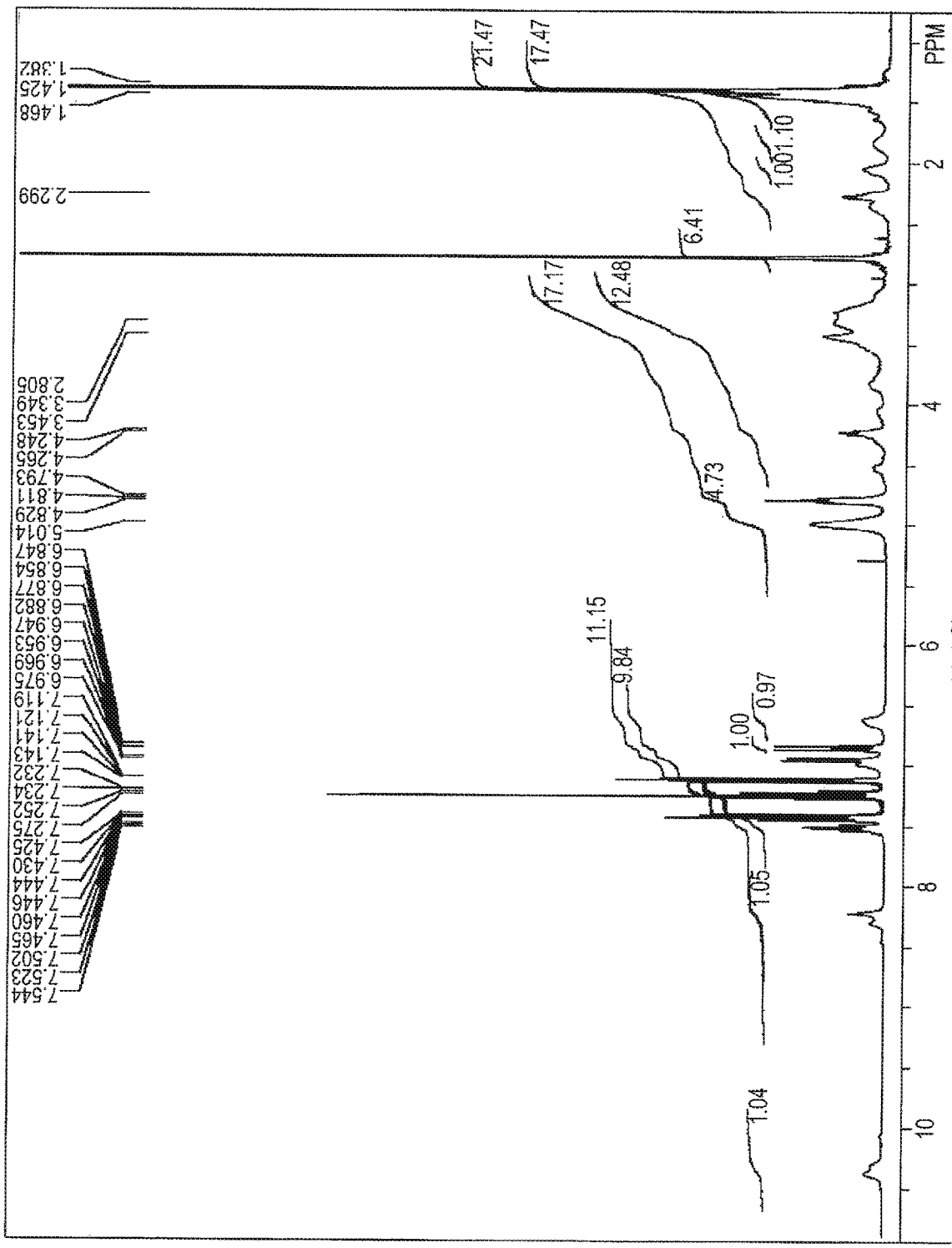

A representative 1HNMR spectrum of dimesylate salt of compound (I) having an E/Z ratio of about 9/1 prepared in cyclohexane in CDCl₃ according to Example 4 is shown in FIG. 4B.

Figure 4C:
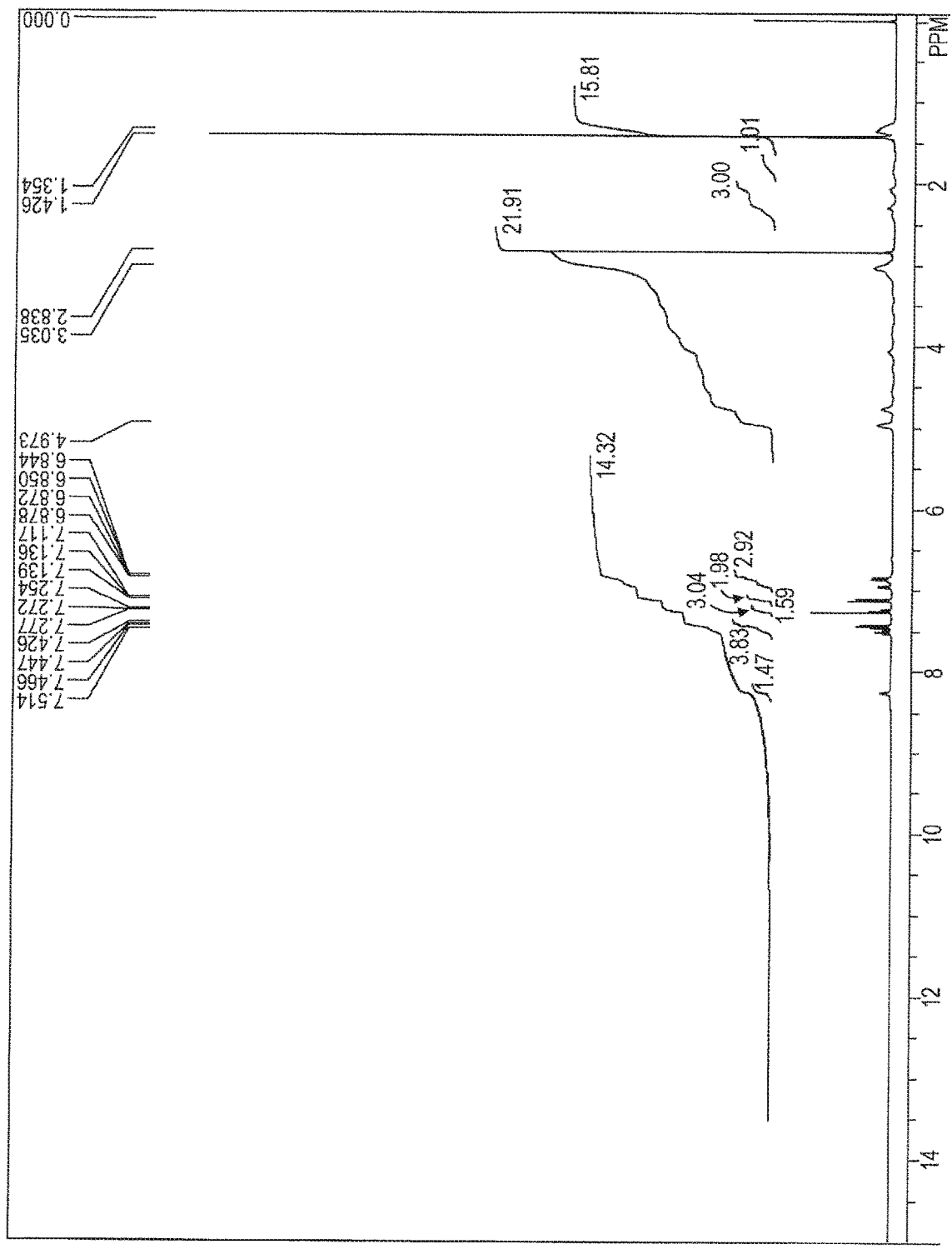

A representative 1HNMR spectrum of mono-methanesulfonic salt of compound (I) having an E/Z ratio of about 9/1 in cyclohexane in CDCl₃ prepared according to Example 4 is shown in FIG. 4C.

Figure 5:
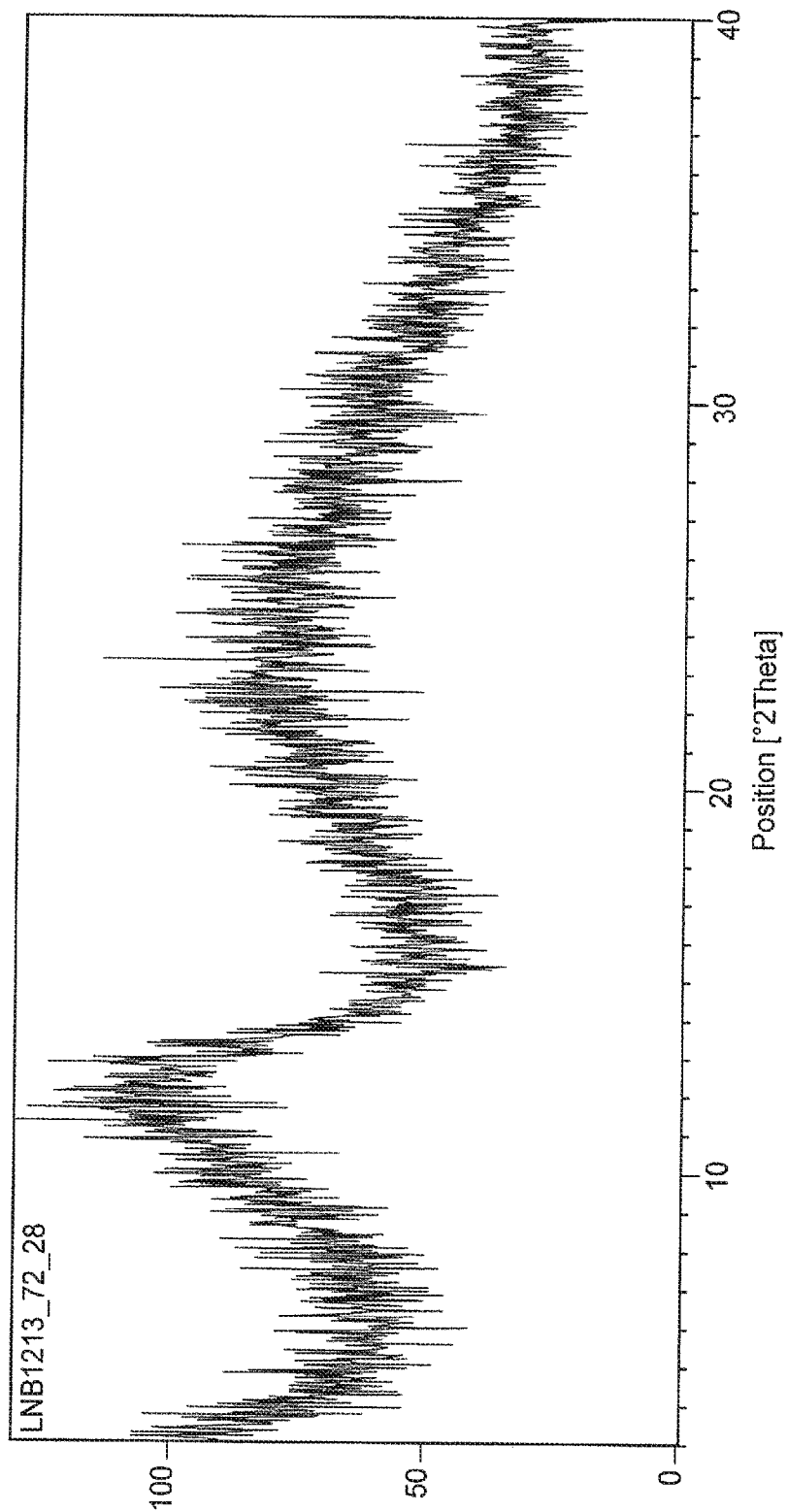

A representative XRPD diffractogram for oxalic acid salt of compound (I) having an E/Z ratio of about 9/1 prepared in isopropyl acetate according to Example 5 is shown in FIG. 5.

Figure 5A:
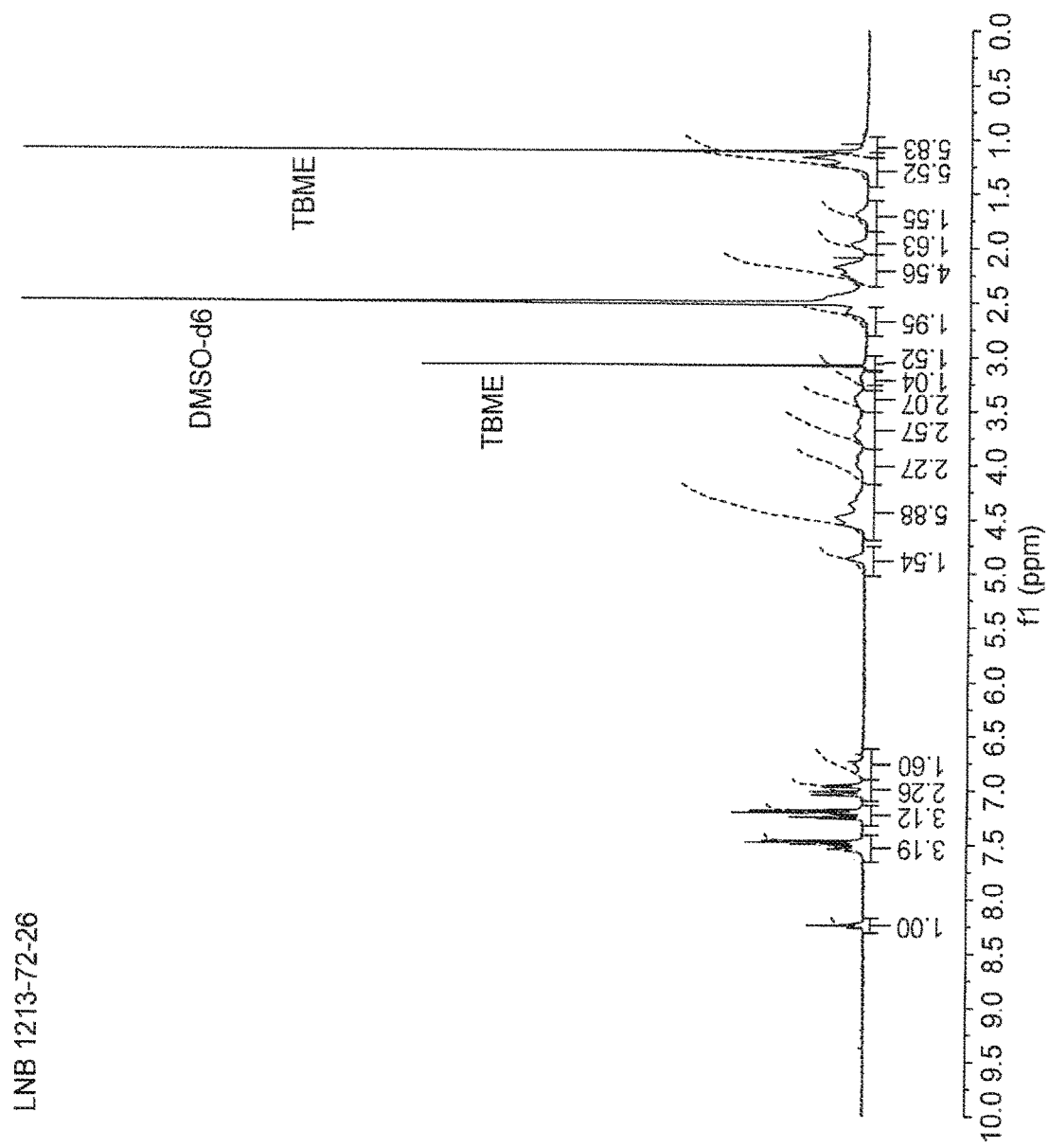

A representative 1H-NMR spectrum of potential (1:1) oxalic acid salt of compound (I) having an E/Z ratio of about 9/1 prepared according to Example 5 is shown in FIG. 5A below.

Figure 6:
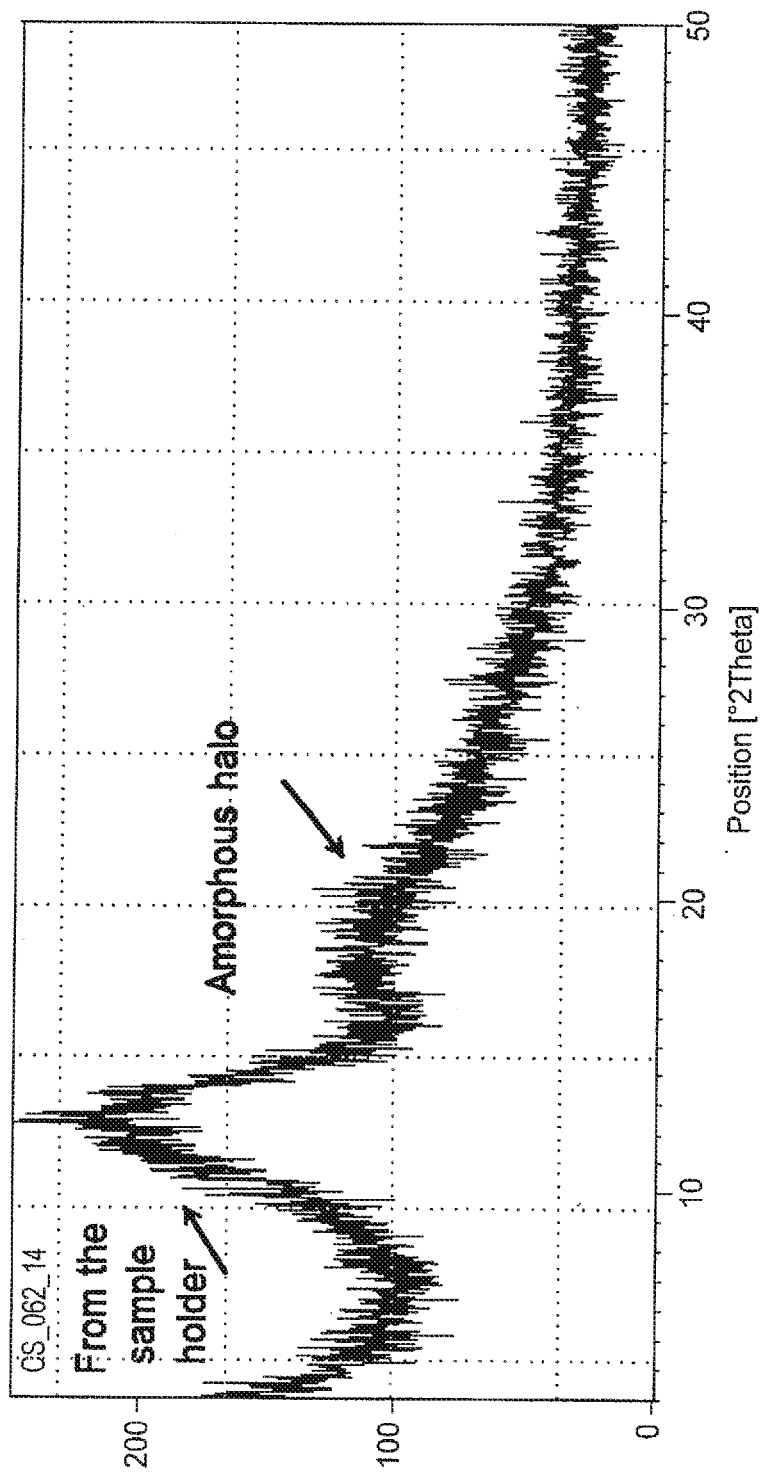
Figure 7:
Figure 7A:
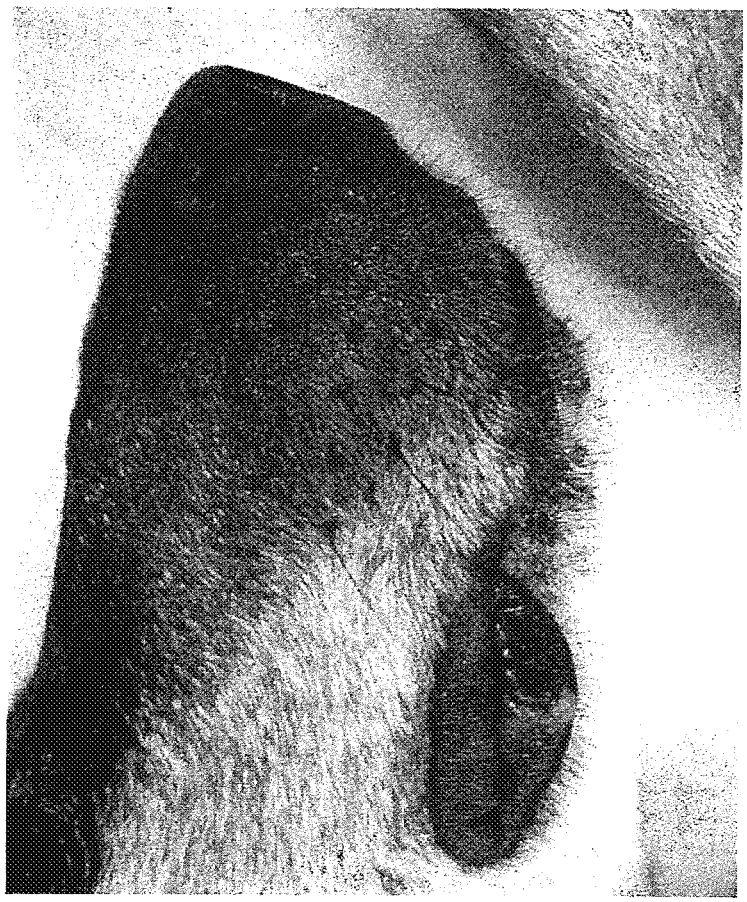
Figure 8:
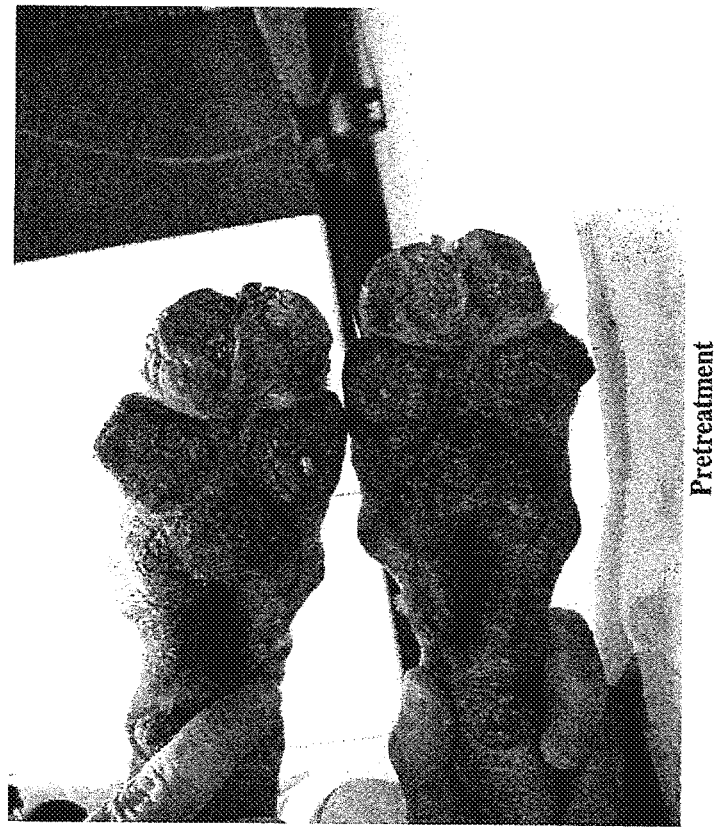
Figure 8A:
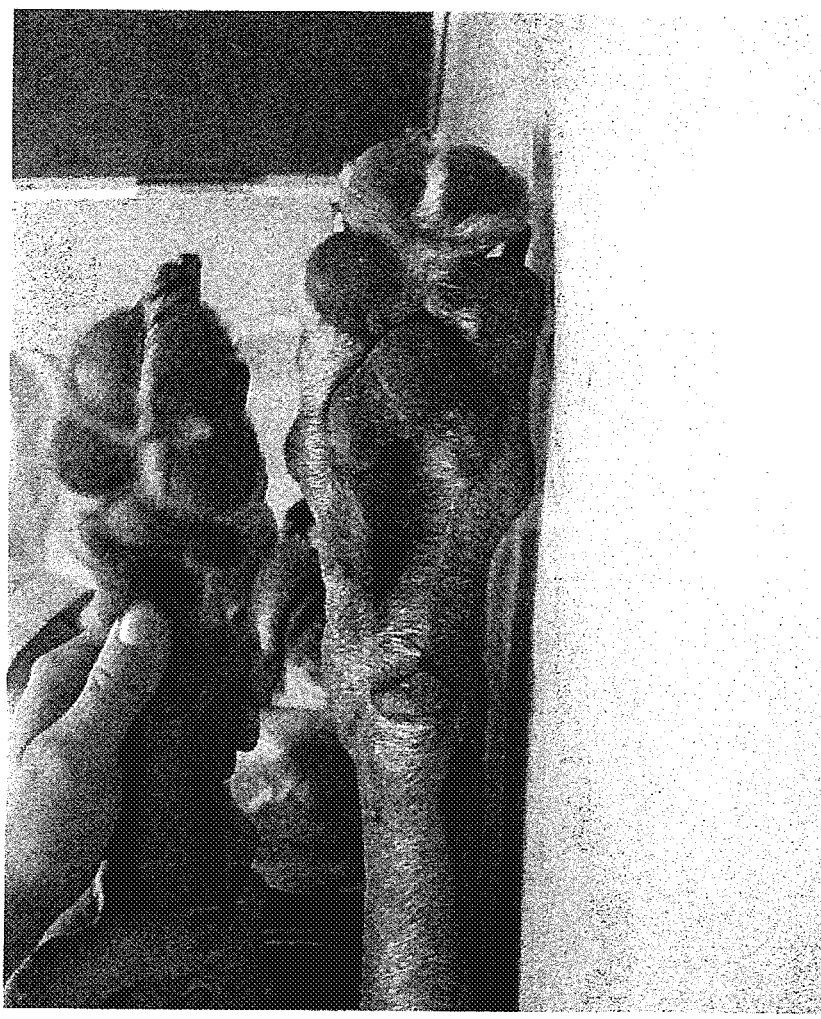

A representative XRPD diffractogram for citric acid salt of compound (I) having an E/Z ratio of about 9/1 prepared according to Example 6 is shown in FIG. 6.

Results from dog pemphigus foliaceus study conducted as described in Example 7 are shown in FIGS. 7, 7A, 8, and 8A below.

DEFINITIONS

Unless otherwise stated, the following terms used in the specification and claims are defined for the purposes of this Application and have the following meaning. All undefined technical and scientific terms used in this Application have the meaning as commonly understood by one of ordinary skill in the art to which this invention belongs.

"Amorphous form" denotes a solid which does not possess a distinguishable crystal lattice and the molecular arrangement of molecules lack a long range order characteristic of a crystal. In particular amorphous denotes a material that does not show a sharp Bragg diffraction peak.

"Compound (I)" as used herein means, unless stated otherwise, E isomer, Z isomer, or a mixture of (E) and (Z) isomers of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile having the structure:

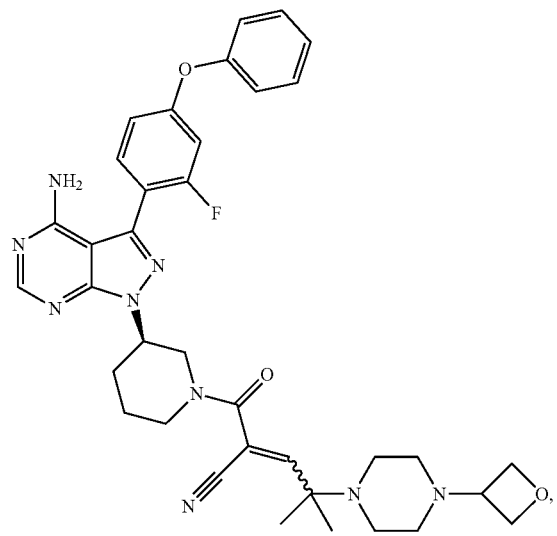 [SMILES: CC(C)(C=C(C#N)C(=O)N1CCC[C@@H](n2nc(-c3ccc(Oc4ccccc4)cc3F)c3c(N)ncnc32)C1)N1CCN(C2COC2)CC1]

"Mammal" as used herein means domesticated animals (such as dogs, cats, and horses), and humans. In one embodiment, mammal is a human.

A "pharmaceutically acceptable salt" as used herein means an acid addition salt that is pharmaceutically acceptable and that possesses the desired pharmacological activity of the compound of which the salt is made (hereafter, sometimes referred to as "parent compound"). Such salts include salts, formed with inorganic acids such as hydrochloric acid, hydrobromic acid, sulfuric acid, phosphoric acid, and the like; or formed with organic acids such as formic acid, acetic acid, propionic acid, hexanoic acid, lactic acid, malonic acid, succinic acid, malic acid, maleic acid, fumaric acid, tartaric acid, citric acid, benzoic acid, mandelic acid, methanesulfonic acid, ethanesulfonic acid, 1,2-ethanedisulfonic acid, benzenesulthnic acid, 4-toluenesulfonic acid, and the like.

A "pharmaceutically acceptable carrier or excipient" means a carrier or an excipient that is useful in preparing a pharmaceutical composition that is generally safe, and neither biologically nor otherwise undesirable, and includes a carrier or an excipient that is acceptable for mammalian pharmaceutical use.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure that, when administered to a mammal in need or recognized need of treatment for treating a disease, is sufficient to effect such treatment for the disease. The "therapeutically effective amount" will vary depending on the compound, the disease and its severity, and the age, weight, etc., of the mammal to be treated.

"Antisolvent" is a solvent in which a compound of the disclosure is less soluble.

For all analytical data discussed in this application, it should be noted that specific values depend on many factors, e.g., specific instrument, sample preparation and individual operator. The data obtained by a particular analytical technique with different experiments are "substantially the same" when characteristic data obtained using the same analytical technique (but may be obtained under different conditions or using different instruments) vary within ±10%, ±5% or ±1%. A person of ordinary skill in the art will recognize characteristic data for each particular analytical technique when presented with data obtained by the analysis. For example, characteristic of data of a XRPD are sharp peaks for crystalline solid and amorphous halo for an amorphous solid.

"Substantially free" as used herein refers to a compound (or salt thereof) such as compound (I) wherein at least about 70% by weight of the compound (or salt thereof) is present as the given solid state form. For example, the phrase "amorphous form of a salt of compound (I) substantially free of any crystalline form(s) thereof" refers to a solid state form of a salt of compound (I) wherein more than about 70% by weight of the salt of compound (I) is in amorphous form with the remaining present in a crystalline form. In one embodiment, such compositions contain at least about 80% by weight of a salt of compound (I) is in amorphous form. In another embodiment at least about 85% by weight of a salt of compound (I) is in amorphous form. In yet another embodiment, at least about 90% by weight of a salt of compound (I) is in amorphous form. In yet another embodiment, at least about 95% by weight of a salt of compound (I) is in amorphous form. In yet another embodiment, at least about 97% by weight or about 98% by weight of a salt of compound (I) is in amorphous form. In yet another embodiment, at least about 99% by weight of a salt of compound (I) is in amorphous form. "About" as used herein means + or −5% deviation from the listed value. For example, a composition containing about 70% by weight of a component may contain 66.5% to 73.5% by weight of the component.

The relative amounts of crystalline and/or amorphous forms in a solid mixture can be determined by well known in the art. For example, X-Ray diffraction provides a convenient and practical means for quantitative determination of the relative amounts of crystalline and/or amorphous forms in a solid mixture. X-Ray diffraction is adaptable to quantitative applications because the intensities of the diffraction peaks of a given compound in a mixture are proportional to the fraction of the corresponding powder in the mixture. Although all salts of compound (I) are amorphous, if any crystalline form of compound (I) (or a salt thereof) is present in a mixture, percent composition of crystalline compound (I) (or a salt thereof) in an unknown composition can be determined. Preferably, the measurements are made on solid powder of compound (I) (or a salt thereof). The X-Ray powder diffraction patterns of an unknown composition may be compared to known quantitative standards containing pure crystalline forms, if any, of compound (I) (or a salt thereof) to identify the percent ratio of a particular crystalline form. If amorphous form is the major fraction of the composition, the amount may be further compared to the total weight of the solid subject to analysis. This is done by comparing the relative intensities of the peaks from the diffraction pattern of the unknown solid powder composition with a calibration curve derived from the X-Ray diffraction patterns of pure known samples. The curve can be calibrated based on the X-Ray powder diffraction pattern for the strongest peak from a pure sample of crystalline forms of compound (I) (or a salt thereof). The calibration curve may be created in a manner known to those of skill in the art. For example, five or more artificial mixtures of crystalline forms of compound (I) (or a salt thereof), at different amounts, may be prepared. In a non-limiting example, such mixtures may contain, 2%, 5%, 7%, 8%, and 10% of Compound (I) (or a salt thereof) for each crystalline form. Then, X-Ray diffraction patterns are obtained for each artificial mixture using standard X-Ray diffraction techniques. Slight variations in peak positions, if any, may be accounted for by adjusting the location of the peak to be measured. The intensities of the selected characteristic peak(s) for each of the artificial mixtures are then plotted against the known weight percentages of the crystalline form. The resulting plot is a calibration curve that allows determination of the amount of the crystalline forms of compound (I) (or a salt thereof) in an unknown sample. For the unknown mixture of crystalline and amorphous forms of compound (I) (or a salt thereof), the intensities of the selected characteristic peak(s) in the mixture, relative to an intensity of this peak in a calibration mixture, may be used to determine the percentage of the given crystalline form in the composition, with the remainder determined to be the amorphous material. The overall crystallinity may be determined as follows: % Crystallinity=$(C/A+C-B) \times 100$, where C is area under crystalline peaks, A is area under amorphous halo, and B is background noise due to air scattering, fluorescence, etc.

"Substantially pure" as used herein in connection with an geometric or polymorphic isomeric form refers to a compound (or salt thereof or an amorphous form of a salt thereof) such as compound (I) wherein more than 70% by weight of the compound (or a salt thereof or an amorphous form of a salt thereof) is present as the given isomeric form. For example, the phrase "the salt or amorphous form of the salt of compound (I) is a substantially pure (E) isomer of compound (I)" refers to the salt or amorphous form of the salt of compound (I) having at least about 70% by weight of the salt or amorphous form of the salt of compound (I) being in the (E) isomeric form, and the phrase "the salt or amorphous form of the salt of compound (I) is a substantially pure (Z) isomer of compound (I)" refers to the salt or amorphous form of the salt of compound (I) having at least about 70% by weight of the salt or amorphous form of the salt of compound (I) being in the (Z) isomeric form. In one embodiment, at least about 80% by weight of the salt or amorphous form of the salt of compound (I) is the (E) form or at least about 80% by weight of the salt or amorphous form of the salt of compound (I) is the (Z) form. In another embodiment at least about 85% by weight of the salt or amorphous form of the salt of compound (I) is in the (E) form or at least about 85% by weight of the salt or amorphous form of the salt of compound (I) is in the (Z) form. In yet another embodiment, at least about 90% by weight of the salt or amorphous form of the salt of the compound (I) is in the (E) form or at least about 90% by weight of the salt or amorphous form of the salt of the compound (I) is in the (Z) form. In yet another embodiment, at least about 95% by weight of the salt or amorphous form of the salt of compound (I) is in the (E) form or at least about 95% by weight of the salt or amorphous form of the salt of compound (I) is in the (Z) form. In yet another embodiment, at least about 97% by weight, or about 98% by weight of the salt or amorphous form of the salt of compound (I) is in the (E) form or at least about 97% by weight, or about 98% by weight of the salt or amorphous form of the salt of compound (I) is in the (Z) form. In yet another embodiment, at least about 99% by weight of the salt or amorphous form of the salt of compound (I) is in the (E) form or at least about 99% by weight of the salt or amorphous form of the salt of compound (I) is in the (Z) form. Similar analysis would apply when Compound (I) is present in as substantially pure E or Z isomer. "About" as used herein means + or −5% deviation from the listed value. For example, a composition containing about 70% by weight of a component may contain 66.5% to 73.5% by weight of the component. The relative amounts of (E) and (Z) isomers in a solid mixture can be determined by well known in the art. One such method if disclosed herein below.

"Acute" as used herein means a disease with a rapid onset and/or a short course.

Treatment decisions often follow formal or informal algorithmic guidelines. Treatment options can often be ranked or prioritized into lines of therapy: first-line therapy, second-line therapy, third-line therapy, and so on. First-line therapy is the first therapy that will be tried. Its priority over other options is usually either (1) formally recommended on the basis of clinical trial evidence for its best-available combination of efficacy, safety, and/or tolerability or (2) chosen based on the clinical experience of the physician. If a first-line therapy either fails to resolve the issue or produces intolerable side effects, additional (second-line) therapies may be substituted or added to the treatment regimen, followed by third-line therapies, and so on. Accordingly, "first-line" therapy as used herein means therapy usually given when someone is diagnosed with a particular disease or condition and can be categorized as standard of care.

"Maintenance therapy" as used herein means a therapy, therapeutic regimen, or course of therapy which is administered subsequent to an initial course of therapy administered to a patient with a disease. Maintenance therapy can be used to halt, slow down, or even reverse the progression of the disease, to maintain the improvement in health achieved by the initial treatment and/or enhance the gains achieved by the initial therapy.

"Flares" as used herein means an exacerbation of a chronic disease. Sometimes referred to as a flare-up, a flare occurs when symptoms of a disease that has been present for a time suddenly worsen. For example, in many arthritis conditions the joints can flare with worsening of stiffness, pain, and swelling.

It will be understood by a person of ordinary skill in the art that when a compound is denoted as (R) stereoisomer (e.g., compound (I)), it may contain the corresponding (S) stereoisomer as an impurity i.e., the (S) stereoisomer may be present inless than about 5%, preferably less than 2% by wt.

Administration and Pharmaceutical Composition

In general, the compounds of this disclosure will be administered in a therapeutically effective amount by any of the accepted modes of administration for agents that serve similar utilities. Therapeutically effective amounts of the compounds disclosed herein may range from about 0.01 to about 500 mg per kg mammal body weight per day, which can be administered in single or multiple doses. A suitable dosage level may be about 0.01 to about 250 mg/kg per day, about 0.05 to about 100 mg/kg per day, or about 0.1 to about 50 mg/kg per day, Within this range, the dosage can be about 0.05 to about 0.5, about 0.5 to about 5 or about 5 to about 50 mg/kg per day. Within this range, the dosage can be from about 200 mg to about 350 mg/bid or from 500 mg to 650 mg qd. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount administered of the compound of this disclosure, i.e., compound (I), the sulfonic acid salt of compound (I), carboxylic acid salt of compound (I) or an amorphous form of a pharmaceutically acceptable salt of compound (I) and any embodiments thereof disclosed above, will depend upon numerous factors such as the severity of the disease to be treated, the age and relative health of the mammal, the potency of the compound and/or pharmaceutically acceptable salt thereof being utilized, the route and form of administration, and other factors.

In general, compounds of this disclosure will be administered as pharmaceutical compositions by any one of the following routes: oral, systemic (e.g., transdermal, intranasal or by suppository), topically, or parenteral (e.g., intramuscular, intravenous or subcutaneous) administration. The preferred manner of administration is oral using a convenient daily dosage regimen, which can be adjusted according to the degree of affliction. Compositions can take the form of tablets, capsules, semisolids, powders, sustained release formulations, enteric coated or delayed release formulation, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound disclosed herein in combination with at least one pharmaceutically acceptable excipient such as binders, surfactants, diluents, buffering agents, antiadherents, glidants, hydrophilic or hydrophobic polymers, retardants, stabilizing agents or stabilizers, disintegrants or superdisintegrants, antioxidants, antifoaming agents, fillers, flavors, colors, lubricants, sorbents, preservatives, plasticizers, and sweeteners. Acceptable excipients are non-toxic, aid administration, and do not adversely affect the therapeutic benefit of the compound disclosed herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like, Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols.

The compounds of the present disclosure can also be administered intranasally. Intranasal formulations are known in the art e.g., see U.S. Pat. Nos. 4,476,116, 5,116, 817 and 6,391,452, each of which is incorporated herein by reference. The choice of excipients will depend upon the nature of the nasal dosage form e.g., solutions, suspensions, or powder. For administration by inhalation, the compounds of the present disclosure may be in the form of solutions, suspensions, and powders. These formulations are administered as an aerosol, a mist, or a powder and can be delivered from pressurized packs or a nebulizer with a suitable propellant such as dichlorodifluoromethane, trichlorofluoromethane, nitrogen, carbon dioxide, etc. In the case of a pressurized aerosol, the dosage unit may be determined by providing a valve to deliver a metered amount. Capsules and cartridges for use in an inhaler may be formulated containing a powder mix of the compound disclosed herein and a suitable powder base such as lactose or starch.

Topical formulation can be liquids, suspension, emulsions, and the like, and can be prepared by methods well known in the art. The formulation will contain, on a weight percent (wt %) basis, from about 0.01-99.99 wt % of a compound and/or pharmaceutically acceptable salt disclosed herein based on the total formulation, with the balance being one or more suitable pharmaceutical excipients and can be administered in single or multiple doses. Suitable excipients include polymers, surfactants, buffering or pH adjusting agents, tonicity and osmotic adjusting agent(s), preservatives, and dispersing agents.

Other suitable pharmaceutical excipients and their formulations are described in Remington's Pharmaceutical Sciences, edited by E. W. Martin (Mack Publishing Company, $20^{th}$ ed., 2000).

The level of the compound in a formulation can vary within the full range employed by those skilled in the art. Typically, the formulation will contain, on a weight percent (wt %) basis, from about 0.01-99.99 wt % of a compound disclosed herein based on the total formulation, with the balance being one or more suitable pharmaceutical excipients.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore by those skilled in the art, contemporaneously or sequentially with a compound of the present disclosure. When a compound of the present disclosure is used contemporaneously with one or more other drugs, a pharmaceutical composition containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the mammal is suffering from or at risk of suffering from an autoimmune disease, an inflammatory disease, or an allergy disease, a compound of present disclosure can be used in with one or more of the following therapeutic agents in any combination: immunosuppressants (e.g., tacrolimus, −37-iethylstilb, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, rninocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, and anticholinergics.

Where the mammal is suffering from or at risk of suffering from a B-cell proliferative disorder (e.g., plasma cell myeloma), the mammal can be treated with a compound disclosed herein in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and docetaxol, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound disclosed herein include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound disclosed herein include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroinan; piposulfan; piroxantrone hydrochloride; plicamycin; plomestane; porfimer sodium; porfiromycin; prednimustine; procarbazine hydrochloride; puromycin; puromycin hydrochloride; pyrazothrin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound and/or pharmaceutically acceptable salt disclosed herein include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; ca.lphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyciopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; clolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ga.nirelix; gelatinase inhibitors; gemcitabine; glutathione inhibitors; hepsulfam; heregulin; hexamethylene bisacetamide; hypericin; ihandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; rnitonafide; mitotoxin fibroblast growth factor-saporin; mitoxantrone; mofarotene; molgramostim; monoclonal antibody, human chorionic gonadotrophin; monophosphoryl lipid A+-40-iethylstilhe cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline;

N-substituted benzamides; nafarelin; nagrestip; naloxone+ pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; patnidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; pla.cetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; rarnosetron; ras farnesyl protein transferase inhibitors; ras inhibitors; ras-GAP inhibitor; retelliptine demethylated; rhenium Re 186 etidronate; rhizoxin; ribozymes; $R_{11}$ retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; strornelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thyrnalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound disclosed herein include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarba.zine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound disclosed herein include but are not limited to vinca alkaloids (e.g., –41-iethylstil, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound disclosed herein include, but are not limited to, nitrogen mustards (e.g., mechloroethamine, cyclophosphamide, chlorambucil, melphalan, etc.), ethylenimine and methylmelamines (e,g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination with a compound disclosed herein include, but are not limited to, adrenocorticosteroids (e.g., prednisone), progestins (e.g., hydroxyprogesterone caproate, megestrol acetate, medroxyprogesterone acetate), estrogens (e,g., –42-iethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a compound of the present disclosure include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BST-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/ Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPINET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica). Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the mammal is suffering from or at risk of suffering from a thromboembolic disorder (e.g., stroke), the mammal can be treated with a compound disclosed herein in any combination with one or more other anti-thromboembolic agents, Examples of anti-thromboembolic agents include, but are not limited to, any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Experimentals

Methods of Analysis $^1$H-NMR experiments were performed on a Bruker AV400 ($^1$H frequency: 400 MHz). $^1$H-NMR experiments of each sample were performed in DMSO-$d_6$ or CDCl$_3$ and each sample was prepared to ca. 5 mg/mL concentration.

Ion chromatography was conducted on Dioned ICS-3000 ion chromatograph equipmed with Dionex Ionpac AS11-HC, 4×250 mm column with AG11-HC colum guard at 1.5 ml/min at 30° C. The eluent was 5 mM NaOH. Ions were detected using a conductivity detector.

The XRPD analysis was carried out on a Siemens D5000 diffractometer, scanning the samples between 3 and 30° 2-theta (between 3 and 50° 2-theta when analysing input materials) with Cu K-alpha radiation source. The material was gently compressed onto a glass disc inserted into an XRPD sample holder. The samples were then loaded into the diffractometer running in reflection mode and analysed.

High Performance Liquid Chromatograophy (HPLC) was conducted on Agilent 1100 equipped with a column heater, gradient elution capability, an autosampler and a UV detector. The column was Zorbax SB-Phenyl at 40° C. and a eluent was water/methanol gradient with 0.1% methane sulfonic acid and UV detection at 225 nm. Total run time was 8 minutes. The following gradient was used (A is water, and B is methanol):

| Minutes | % A | % B |
| --- | --- | --- |
| 0.0 | 40 | 60 |
| 5.0 | 20 | 80 |
| 7.0 | 20 | 80 |
| 7.25 | 40 | 60 |
| 8.0 | 40 | 60 |

EXAMPLE 1

Synthesis of 2-[(3R)-3-[4-amino-3-(2-fluoro-4-phenoxy-phenyl)pyrazolo[3,4-d]pyrimidin-1-yl]-piperidine-1-carbonyl]-4-methyl-4-[4-(oxetan-3-yl)piperazin-1-yl]pent-2-enenitrile

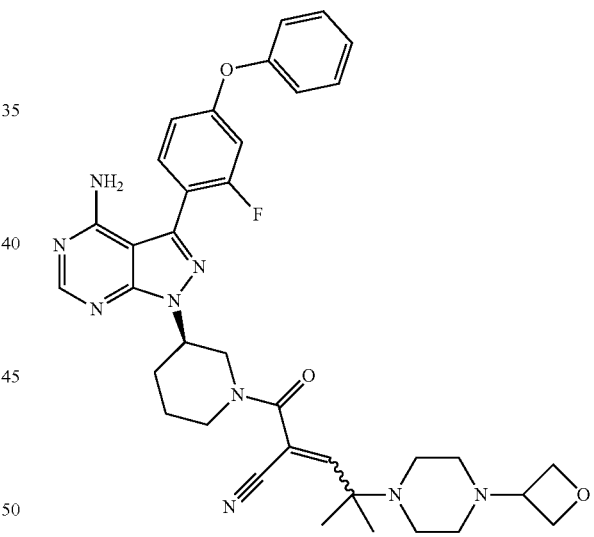

Step 1

To a solution of 3-[(3R)-3-[4-amino-3-(2-fluoro-4-phenoxy-phenyl)pyrazolo[3,4-d]pyrimidin-1-yl]-1-piperidyl]-3-oxo-propanenitrile (15 g, 3.12 mmol), 2-methyl-2-[4-(oxetan-3-yl)piperazin-1-yl]propanal (794.25 mg, 3.74 mmol) in DCM (40 mL), pyrrolidine (1.54 mL,18.71 mmol) at 0-5° C. was added, which is followed by TMS-Cl (1.58 mL, 12.47 mmol). The reaction mixture was stirred at 0-5° C. for 3 h and was quenched with 1 M potassium phosphate buffer (pH 3). Layers were separated and the organic layer was washed once more with 1 M potassium phosphate buffer (pH 3). The organic layer was extracted with 1 M potassium Phosphate buffer at pH 1.5. Layers were separated. The aqueous phase contained the desired product while the impurities stayed in the organic phase. The aqueous phase was neutralized with 1 M potassium phosphate (pH 7) and was extracted with isopropylacetate (10 volumes). Upon concentration 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile was obtained as a foam having >99% HPLC purity. MS (pos. ion) in/z: 666 (M+1).

The foam containing high levels of residual solvent was dissolved in 2 M HCl and the resulting solution was placed under vacuum to remove residual organic solvents. pH of the solution was then adjusted to ~7 and the resulting paste was filtered and dried in vacuum without heat. This resulted in isolation of 2-[(3R)-3-[4-amino-3-(2-fluoro-4-phenoxy-phenyl)pyrazolo[3,4-d]pyrimidin-1-yl]peridine-1-carbonyl]-4-methyl-4-[4-(oxetan-3-yl)piperazin-1-yl]pent-2-enenitrile containing reidual water up to 10%. Drying under vacuum without heat reduces the water level but lead to generation of impurities.

Step 1A

Alternatively, the isopropylacetate solution of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile can be concentrated to 4 vol and added to heptane (20 volume) at 0° C. The resulting suspension was stirred at 0° C. overnight and the product was filtered, washed twice with heptane and dried at 45° C. for 2 days under vacuum to give 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile in 85-90% yield as a free flowing solid. However, the solids obtained by this method contained high residual solvents (3.9 wt % isopropylacetate and 1.7 wt % heptane). In addition, the free base form was not very stable as degradation products were observed during the drying process at less than 45° C.

Salt formation

EXAMPLE 2

Preparation of 2-[(3R)-3-[4-amino-3-(2-fluoro-4-phenoxy-phenyl)-pyrazolo[3,4-d]pyrimidin-1-yl]piperidine-1-carbonyl]-4-methyl-4-[4-(oxetan-3-yl)-piperazin-1-yl]pent-2-enenitrile hemisulfate and sulfate salt Hemisulfate:

To the solution of 2-[(3R)-3-[4-amino-3-(2-fluoro-4-phenoxy-phenyl)pyrazolo[3,4-d]pyrimidin-1-yl]-piperidine-1-carbonyl]-4-methyl-4-[4-(oxetan-3-yl)-piperazin-1-yl]pent-2-enenitrile (4.2 g) in EtOAc (60 mL, 15 vol) was added sulfuric acid (0.31 g, 0.17 mL, 0.5 eq) in EtOAc (20 mL, 5 vol) at ambient temperature. The suspension was stirred at ambient temperature for ~2 hr and then 40° C. for 4 hr and then at ambient temperature for at least 1 hr. After filtration and drying at ambient temperature under vacuum, 1.5 g of white powder was obtained. Solubility of the hemi-sulfate at ambient temperature was >100 mg/mL in water.

Sulfate Salt

To the solution of 2-[(3R)-3-[4-amino-3-(2-fluoro-4-phenoxy-phenyl)-pyrazolo[3,4-d]pyrimidin-1-yl]-piperidine-1-carbonyl]-4-methyl-4-[4-(oxetan-3-yl)-piperazin-1-yl]pent-2-enenitrile (810 mg) in EtOAc (8 mL, 10 vol) was added sulfuric acid (0,06 g, 1.0 equiv.) in EtOAc (2.5 mL, 5 vol) at ambient temperature. The resulting suspension was stirred at 40° C. for 2 hr and then cooled to ambient temperature for at least 1 hr. After filtration, solids were dried by suction under Argon for 1 h to give a white powder (0.68 g) in 69% yield.

| Salt form | Solvent | XRD | 1H NMR |
|---|---|---|---|
| H$_2$SO$_4$ | EtOAc | Amorphous | Consistent withstructure |
| 0.5 H$_2$SO$_4$ | EtOAc | Amorphous | Consistent with structure |

EXAMPLE 3

Preparation of 2-[(3R)-3-[4-amino-3-(2-fluoro-4-phenoxy-phenyl)-pyrazolo[3,4-d]pyrimidin-1-yl]-piperidine-1-carbonyl]-4-methyl-4-[4-(oxetan-3-yl)-piperazin-1-yl]pent-2-enenitrile hydrochloride To a solution of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (100 mg, 0.15 mmol) in CH$_2$Cl$_2$ (1 ml) at ambient temperature was added 2 equivalent of HCl (0.3 mmol, 0.15 ml of 2M HCl in 1:1 dioxane:CH$_2$Cl$_2$). The resulting homogeneous solution was stirred at ambient temperature for 1 h and was added dropwise to 15 volumes of ethylacetate (as compared to CH$_2$Cl$_2$) resulting in formation of a white solid. The mixtures was aged at ambient temperature for 1 h and placed at 2-8 C for 19 h. Upon filtration and washing of the filter cake with ethylacetate and drying a white solid was obtained. Analysis by XRPD indicated formation of an amorphous solid. Both $^1$H-NMR and IC analysis indicated formation of the salt. IC indicated formation mono-HCl salt.

| Salt form | Solvent | Antisolvent | XRPD | 1H NMR |
|---|---|---|---|---|
| HCl | CH$_2$Cl$_2$ | EtOAc | Amorphous | Consistent with structure |

EXAMPLE 4

General procedure for preparation of 2-[(3R)-3-[4-amino-3-(2-fluoro-4-phenoxy-phenyl)pyrazolo[3,4-d]pyrimidin-1-yl]-piperidine-1-carbonyl]-4-methyl-4-[4-(oxetan-3-yl)-piperazin-1-yl]pent-2-enenitrile mono- and di-mesylate salts To a solution of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (100 mg, 0.15 mmol) in CH$_2$Cl$_2$ (1 ml) at ambient temperature was added either 1 equivalent of methanesulfonic acid (0.15 mmol, 0.2 ml of 74 mg/ml solution in CH$_2$Cl$_2$) or 2 equivalent of methanesulfonic acid (0.3 mmol, 0.4 ml of 74 mg/ml solution in CH2Cl$_2$). The resulting homogeneous solution was stirred at ambient temperature for 1 h and was added dropwise to 10 volumes of antisolvents (ethylacetate, methyl tert-butylether (MTBE), or cyclohexane) (10 ml as compared to CH$_2$Cl$_2$) resulting in formation of a white solid. The mixture was aged at ambient temperature for 1h and placed at 2-8° C. for 19 h. Upon filtration and washing of the filter cake with the antisolvent and drying, a white solid was obtained. Analysis by XRPD indicated formation of an amorphous solid. Both $^1$H-NMR and IC analysis indicated formation of the salt as well as counterion ratio.

Alternatively 2-[(3R)-3-[4-amino-3-(2-fluoro-4-phenoxy-phenyl)pyrazolo[3,4-d]-pyrimine-1-yl]piperidine-1-carbonyl]-4-methyl-4-[4-(oxetan-3-yl)piperazin-1-yl]pent-2-enenitrile can be dissolved in 4 volumes of isopropylacetate and added to 2 equivalent of methanesulfonie acid in 6 volumes of isopropylacetate at 0° C. to generate the dimesylate salt.

| Salt form | Solvent | Antisolvent | XRPD | IC-mesylate content[1] | $^1$H-NMR |
|---|---|---|---|---|---|
| 2MSA | CH$_2$Cl$_2$ | EtOAc | Amorphous | ND | Consistent with 2:1 salt |
| MSA | CH$_2$Cl$_2$ | EtOAc | Amorphous | 12.5% | Consistent with 1:1 salt |
| 2MSA | CH$_2$Cl$_2$ | MTBE | Amorphous | 22.8% | Consistent with 2:1 salt |
| MSA | CH$_2$Cl$_2$ | MTBE | Amorphous | 14.8% | Consistent with 1:1 salt |
| 2MSA | CH$_2$Cl$_2$ | Cyclohexane | Amorphous | 21.8% | Consistent with 2:1 salt |
| MSA | CH$_2$Cl$_2$ | Cyclohexane | Amorphous | 13.9% | Consistent with 1:1 salt |
| 2MSA | IPAC | — |  | ND | Consistent with 2:1 salt |

[1]Theoretical mesylate content, monomesylate = 12.6% and dimesylate = 22.4%, ND = not determined

EXAMPLE 5

General Procedure for the Preparation of Carboxylate Salt

Approximately 20 mg of the compound (I) was dissolved in minimum amount of the allocated solvent system. These were then mixed with the appropriate number of equivalents of counterion dissolved or slurried in the allocated solvent.

If compound (I) was insoluble in the selected solvent, slurry of the sample was used after adding 300 µL.

If the acid was insoluble in the selected solvent, slurry of the acid was used after adding 300 µL.

If the acid was a liquid, the acid was added to the dissolved/slurried compound (I) from a stock solution in the allocated solvent.

The suspensions/precipitates resulting from the mixtures of compound (I) were temperature cycled between ambient (ca. 22° C.) and 40° C. in 4 hour cycles for ca. 48 hrs (the cooling/heating rate after each 4 hour period was ca. PC/min). The mixtures were visually checked and any solids present were isolated and allowed to dry at ambient conditions prior to analysis. Where no solid was present, samples were allowed to evaporate at ambient, Samples which produced amorphous material, after the treatment outlined above, were re-dissolved and precipitated using anti-solvent (tert-butylmethylether) addition methods at ambient conditions (ca. 22° C.). i.e. the selected anti-solvent was added to each solution, until no further precipitation could be observed visually or until no more anti-solvent could be added. The solvents used in this preparation were acetonitrile, acetone, isopropyl acetate, THF and MTBE. The acid used were oxalic acid, L-aspartic acid, maleic acid, malonic acid, L-tartaric acid, and fumaric acid.

EXAMPLE 6

General procedure for preparation of 2-[(3R)-3-[4-amino-3-(2-fluoro-4-phenoxy-phenyl)pyrazolo[3,4-d]pyrimidin-1-yl]-piperidine-1-carbonyl]-4-methyl-4-[4-(oxetan-3-yl)-piperazin-1-yl]pent-2-enenitrile hemicitrate salt To a solution 2-[(3R)-3-[4-amino-3-(2-fluoro-4-phenoxy-phenyl)pyrazolo[3,4-d]-pyrimidin-1-yl]piperidine-1-carbonyl]-4-methyl-4-[4-(oxetan-3-yl)piperazi n-1-yl]pent-2-enenitrile (5 g, 7.5 mmol) in ethanol (50 ml) was added citric acid (720.5 mg, 3.76 mmol) dissolved in 2 ml of water. Mixture was stirred at ambient temperature for 15 min, additional 0.5 ml of water was added and the mixture was stirred for 1 h, concentrated in vacuo to a gum. Ethanol was added and the mixture was concentrated. This process was repeated twice more and then CH$_2$Cl$_2$ was added to the mixture. Upon concentration a white solid was obtained which was tumble dried under reduced pressure at 40 C for 4 h, then in a vacuum oven for 19 h to give 5,4 g of a solid. Analysis by XRD indicated formation of an amorphous solid.

EXAMPLE 7

Dog Pemphigus Foliaceus Study

A 30 kg Doberman dog with a characteristic first presentation of pemphigus folliaceus on the nose and paws was administered an oral dose of 500 mg daily of the BTK inhibitor (R,E)-2-(3-(4-amino-3-(2-fluoro-4-phenoxy-phenyl)-1H-pyrazolo[3,4-d]-pyrimidin-1-yl)piperidine-1-carbonyl)-4,4-dimethylpent-2-enenitrile instead of the usual treatment for pemphigus of high dose corticosteroids (typically 1-2 mg/kg). This dose resulted in a level of BTK occupancy 24 hours after each dose of approximately 70% as confirmed by blood taken 24 hours after the first dose.

The dog responded clinically to the drug as a monotherapy within three days, with improved eating and ambulation noted by the owner. At the one week follow up visit both owner and observing veterinarian reported improved general health and commencement of pemphigus lesion healing. The observing veterinarian commented that the improvement was "just like with corticosteroids" and recommended that corticosteroid therapy did not need to be commenced. No well-known corticosteroid-like adverse effects in canines, such as polyuria, polydipsia, polyphagia or weight gain, were noted.

After two weeks of treatment, the general health of the dog was excellent and skin lesions continued to improve. By four weeks, skin lesions had completely healed (see FIGS. 7, 7A, 8, and 8A).

The surprising conclusion of this experiment is that adequate doses of a BTK inhibitor are effective and safe as the acute treatment for pemphigus folliaceus in a dog, replacing the need for corticosteroid therapy.

As shown in Table 3, dog PF and human PV share many similar characteristics that make generalization of treatment effects for human disease from observations of the dog disease credible.

TABLE 3

Comparison of dog pemphigus foliaceus (PF) and human pemphigus vulgaris (PV)

| Naturally occurring autoimmune blistering disease | Dog PF | Human PV |
|---|---|---|
| Autoantigens to epidermal proteins | ✓ | ✓ |
| Never resolves spontaneously | ✓ | ✓ |
| Mainstay of treatment high dose corticosteroids | ✓ | ✓ |
| Early disease response to corticosteroids 1-2 weeks | ✓ | ✓ |
| Full disease control with corticosteroids takes 4-12 weeks | ✓ | ✓ |
| Relapses without maintenance treatment | ✓ | ✓ |
| High mortality in first year, partly presumed due to high dose corticosteroids | ✓ | ✓ |

In addition, the ability of (R, E)-2-(3-(4-amino-3-(2-fluoro-4-phenoxyphenyl)-1H-pyrazolo[3,4-d]-pyrimidin-1-yl)piperidine-1-carbonyl)-4,4-dimethylpent-2-enenitrile to rapidly control dog PF suggests that adequate doses of a BTK inhibitor can replace corticosteroids not just in human PV but in other diseases where corticosteroids are used acutely.

Formulation Examples

The following are representative pharmaceutical formulations containing a compound disclosed herein.

Parenteral Composition

To prepare a parenteral pharmaceutical composition suitable for administration by injection, 100 mg of a compound disclosed herein is dissolved in 2% HPMC, 1% Tween 80 in DI water, pH 2.2 with MSA, q.s. to at least 20 mg/mL. The mixture is incorporated into a dosage unit form suitable for administration by injection.

Oral Composition

To prepare a pharmaceutical composition for oral delivery, 400 mg of a compound disclosed herein and the following ingredients are mixed intimately and pressed into single scored tablets.

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Inhalation Composition

To prepare a pharmaceutical composition for inhalation delivery, 20 mg of a a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of of a salt of a compound disclosed herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical opthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μl of spray for each application.

What is claimed:

1. A method of treating lupus nephritis in a mammal comprising administering to the mammal a pharmaceutical composition comprising:
    a compound selected from (E) isomer, (Z) isomer, and a mixture of (E) and (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile; or
    a pharmaceutically acceptable salt of any of the foregoing compounds.

2. The method of claim 1, wherein the pharmaceutical composition comprises at least one compound which is a substantially pure (E) or (Z) isomer of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, and/or
    at least one pharmaceutically acceptable salt of the compound; and
    at least one pharmaceutically acceptable carrier or excipient.

3. The method of claim 2, wherein at least about 85% w/w of 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile or at least about 85% w/w of a pharmaceutically acceptable salt of 2-[(3R)-3[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile is the (E) isomer.

\* \* \* \* \*

UNITED STATES PATENT AND TRADEMARK OFFICE
CERTIFICATE OF CORRECTION

| | |
|---|---|
| PATENT NO. | : 11,369,613 B2 |
| APPLICATION NO. | : 17/063061 |
| DATED | : June 28, 2022 |
| INVENTOR(S) | : Mohammad R. Masjedizadeh and Steven Gourlay |

It is certified that error appears in the above-identified patent and that said Letters Patent is hereby corrected as shown below:

On the Title Page

Please delete the title page and replace it with the attached title page.

In the Claims

In Column 42, Line 56, insert --2. The method of claim 1, wherein the mammal is a human.--.
In Column 42, Line 56, renumber Claim 2 to be Claim 3.
In Column 42, Line 66, change "claim 2" to --claim 3--.

Signed and Sealed this
Seventh Day of November, 2023

Katherine Kelly Vidal
*Director of the United States Patent and Trademark Office*

(12) United States Patent
Masjedizadeh et al.

(10) Patent No.: US 11,369,613 B2
(45) Date of Patent: Jun. 28, 2022

(54) SALTS AND SOLID FORM OF A BTK INHIBITOR

(71) Applicant: PRINCIPIA BIOPHARMA INC., South San Francisco, CA (US)

(72) Inventors: Mohammad Reza Masjedizadeh, San Jose, CA (US); Steven Gourlay, Queens Park (AU)

(73) Assignee: Principia Biopharma Inc., South San Francisco, CA (US)

(*) Notice: Subject to any disclaimer, the term of this patent is extended or adjusted under 35 U.S.C. 154(b) by 0 days.

(21) Appl. No.: 17/063,061

(22) Filed: Oct. 5, 2020

(65) Prior Publication Data
US 2021/0015821 A1 Jan. 21, 2021

Related U.S. Application Data

(60) Division of application No. 16/596,611, filed on Oct. 8, 2019, now Pat. No. 10,828,307, which is a continuation of application No. 16/116,425, filed on Aug. 29, 2018, now Pat. No. 10,456,403, which is a continuation of application No. 15/120,293, filed as application No. PCT/US2015/016963 on Feb. 20, 2015, now Pat. No. 10,092,569.

(60) Provisional application No. 62/096,468, filed on Dec. 23, 2014, provisional application No. 61/946,480, filed on Feb. 28, 2014, provisional application No. 61/943,262, filed on Feb. 21, 2014.

(51) Int. Cl.
*A61K 31/519* (2006.01)
*A61K 31/5395* (2006.01)
*A61P 25/00* (2006.01)
*A61K 45/06* (2006.01)
*C07D 487/04* (2006.01)

(52) U.S. Cl.
CPC ........ *A61K 31/519* (2013.01); *A61K 31/5395* (2013.01); *A61K 45/06* (2013.01); *A61P 25/00* (2018.01); *C07D 487/04* (2013.01)

(58) Field of Classification Search
CPC ...... A61K 31/519; C07D 487/04; A61P 35/00
USPC .......................................... 514/262.1; 544/262
See application file for complete search history.

(56) References Cited

U.S. PATENT DOCUMENTS

| | | |
|---|---|---|
| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,828,426 B2 | 9/2014 | Shah et al. |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens et al. |
| 9,994,576 B2 | 6/2018 | Owens et al. |
| 10,092,569 B2 | 10/2018 | Masjedizadeh et al. |
| 10,456,403 B2 | 10/2019 | Masjedizadeh et al. |
| 10,485,797 B2 | 11/2019 | Gourlay |
| 10,533,013 B2 | 1/2020 | Owens et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |

(Continued)

FOREIGN PATENT DOCUMENTS

| | | |
|---|---|---|
| CN | 1274280 A | 11/2000 |
| CN | 1681483 A | 10/2005 |

(Continued)

OTHER PUBLICATIONS

2012 ICD-9-CM Diagnosis Code 372.30: Conjunctivitis, unspecified, retrieved Aug. 4, 2016 (1 page).

(Continued)

*Primary Examiner* — Jeffrey H Murray
(74) *Attorney, Agent, or Firm* — McNeill Baur PLLC

(57) ABSTRACT

Disclosed herein are processes for preparing 2-[(3R)-3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile free base (compound (I)), salts of compound (I) and solid state form of said salts. Also disclosed herein are pharmaceutical compositions comprising such salts and solid state form thereof and methods of treating cancer, autoimmune, and inflammatory diseases using compound (I) or a pharmaceutically acceptable salt thereof.

3 Claims, 17 Drawing Sheets